(12) United States Patent
Krstajic et al.

(10) Patent No.: US 12,133,634 B2
(45) Date of Patent: Nov. 5, 2024

(54) ENDOSCOPIC IMAGING APPARATUS AND METHOD

(71) Applicant: The University Court of the University of Edinburgh, Edinburgh (GB)

(72) Inventors: Nikola Krstajic, Edinburgh (GB); Kev Dhaliwal, Edinburgh (GB)

(73) Assignee: THE UNIVERSITY COURT OF THE UNIVERSITY OF EDINBURGH, Edindurgh (GB)

( * ) Notice: Subject to any disclaimer, the term of this patent is extended or adjusted under 35 U.S.C. 154(b) by 1049 days.

(21) Appl. No.: 16/091,786

(22) PCT Filed: Apr. 6, 2017

(86) PCT No.: PCT/GB2017/050975
§ 371 (c)(1),
(2) Date: Oct. 5, 2018

(87) PCT Pub. No.: WO2017/174998
PCT Pub. Date: Oct. 12, 2017

(65) Prior Publication Data
US 2019/0159663 A1 May 30, 2019

(30) Foreign Application Priority Data
Apr. 6, 2016 (GB) .................................. 1605873

(51) Int. Cl.
*A61B 1/04* (2006.01)
*A61B 1/00* (2006.01)
(Continued)

(52) U.S. Cl.
CPC ........ *A61B 1/043* (2013.01); *A61B 1/000094* (2022.02); *A61B 1/0005* (2013.01);
(Continued)

(58) Field of Classification Search
None
See application file for complete search history.

(56) References Cited

U.S. PATENT DOCUMENTS 4,213,462 A * 7/1980 Sato .................... A61B 5/0064
600/477
5,736,410 A * 4/1998 Zarling ................. B82Y 15/00
436/63

(Continued)

FOREIGN PATENT DOCUMENTS

FR 2852394 A1 9/2004
FR 2865369 A1 7/2005

OTHER PUBLICATIONS

International Searching Authority, International Search Report and Written Opinion for International Application No. PCT/GB2017/050975, dated Jul. 25, 2017, 14 pages, European Patent Office, Netherlands.

(Continued)

*Primary Examiner* — Timothy J Neal
*Assistant Examiner* — James Edward Boice
(74) *Attorney, Agent, or Firm* — Alston & Bird LLP

(57) ABSTRACT

An endoscopic imaging apparatus comprises at least one light source (1, 2, 3) configured to provide excitation signals to an imaging region via a common transmission path. Each excitation signal has one of a plurality of different colours. A controller (100) is configured to control the at least one light source (1, 2, 3) to provide the excitation signals as a repeating time-interleaved sequence that comprises at least an excitation signal of a first one of the colours and a subsequent excitation signal of a second one of the colours. A monochrome detector (80) is configured, for each of at least some of the excitation signals, to receive at least part of a respective response signal emitted from the imaging (Continued)

region in response to the excitation signal and to generate image data based on the at least part of the response signal.

23 Claims, 15 Drawing Sheets

(51) Int. Cl.
*A61B 1/06* (2006.01)
*A61B 1/07* (2006.01)
*A61B 5/00* (2006.01)
(52) U.S. Cl.
CPC ............ *A61B 1/042* (2013.01); *A61B 1/0638* (2013.01); *A61B 1/0669* (2013.01); *A61B 1/07* (2013.01); *A61B 5/0071* (2013.01); *A61B 5/0075* (2013.01); *A61B 5/0084* (2013.01); *A61B 1/00186* (2013.01); *A61B 5/7203* (2013.01)

(56) References Cited

U.S. PATENT DOCUMENTS

| | | | | |
|---|---|---|---|---|
| 5,936,730 | A * | 8/1999 | Foley | B01J 19/0046 356/73 |
| 6,259,936 | B1 * | 7/2001 | Boggett | A61B 5/0261 600/475 |
| 6,537,829 | B1 * | 3/2003 | Zarling | B82Y 15/00 436/805 |
| 7,328,059 | B2 * | 2/2008 | Sevick-Muraca | A61B 5/415 600/431 |
| 7,599,732 | B2 * | 10/2009 | Sevick-Muraca | G01N 21/6428 60/473 |
| 7,865,230 | B1 * | 1/2011 | Sevick-Muraca | A61B 5/418 600/476 |
| 8,348,430 | B2 * | 1/2013 | Artsyukhovich | A61B 3/0008 351/221 |
| 8,977,331 | B2 * | 3/2015 | Kim | A61B 90/37 382/128 |
| 9,182,252 | B2 * | 11/2015 | Dubin | G01B 11/14 |
| 2005/0018185 | A1 | 1/2005 | Genet et al. | |
| 2005/0078924 | A1 | 4/2005 | Viellerobe et al. | |
| 2005/0113641 | A1 * | 5/2005 | Bala | A61B 1/0646 600/104 |
| 2005/0143627 | A1 * | 6/2005 | Cline | A61B 1/0638 600/109 |
| 2005/0157981 | A1 | 7/2005 | Berier et al. | |
| 2005/0207668 | A1 | 9/2005 | Perchant et al. | |
| 2005/0242298 | A1 | 11/2005 | Genet et al. | |
| 2006/0056017 | A1 | 3/2006 | Berier et al. | |
| 2006/0256194 | A1 | 11/2006 | Viellerobe et al. | |
| 2007/0177104 | A1 | 8/2007 | Lacombe et al. | |
| 2007/0273930 | A1 | 11/2007 | Berier et al. | |
| 2007/0290145 | A1 | 12/2007 | Viellerobe et al. | |
| 2008/0029711 | A1 | 2/2008 | Viellerobe et al. | |
| 2008/0045848 | A1 | 2/2008 | Lacombe et al. | |
| 2008/0225231 | A1 | 9/2008 | Lacombe et al. | |
| 2008/0231807 | A1 | 9/2008 | Lacombe et al. | |
| 2009/0023999 | A1 | 1/2009 | Mathieu et al. | |
| 2009/0041314 | A1 | 2/2009 | Vercauteren et al. | |
| 2009/0097806 | A1 | 4/2009 | Viellerobe et al. | |
| 2009/0240143 | A1 | 9/2009 | Osdoit et al. | |
| 2010/0168610 | A1 | 7/2010 | Lacombe et al. | |
| 2010/0210904 | A1 * | 8/2010 | Cline | A61B 1/0655 600/109 |
| 2010/0234686 | A1 | 9/2010 | Lacombe et al. | |
| 2010/0296178 | A1 | 11/2010 | Genet et al. | |
| 2011/0015529 | A1 | 1/2011 | Abrat et al. | |
| 2011/0133101 | A1 | 6/2011 | Viellerobe et al. | |
| 2011/0137126 | A1 * | 6/2011 | French | G02B 23/26 600/178 |
| 2011/0254980 | A1 | 10/2011 | Perchant et al. | |
| 2011/0274325 | A1 | 11/2011 | Vercauteren et al. | |
| 2011/0317963 | A1 | 12/2011 | Rocher et al. | |
| 2012/0035484 | A1 | 2/2012 | Thiberville et al. | |
| 2012/0123236 | A1 | 5/2012 | Boularot et al. | |
| 2012/0184842 | A1 | 7/2012 | Boularot et al. | |
| 2013/0321814 | A1 * | 12/2013 | Zhan | G01N 21/6408 250/200 |
| 2014/0023993 | A1 * | 1/2014 | Zeng | A61B 18/18 606/9 |
| 2014/0117207 | A1 | 5/2014 | Savoire et al. | |
| 2014/0171764 | A1 * | 6/2014 | Kim | A61B 1/043 600/317 |
| 2014/0207150 | A1 | 7/2014 | Rosa et al. | |
| 2014/0276008 | A1 * | 9/2014 | Steinbach | A61B 5/0059 600/424 |
| 2015/0057499 | A1 | 2/2015 | Erden et al. | |
| 2015/0104394 | A1 | 4/2015 | Abbaci et al. | |
| 2016/0253801 | A1 | 9/2016 | Linard et al. | |
| 2016/0374562 | A1 * | 12/2016 | Vertikov | A61B 5/0095 600/424 |
| 2018/0249901 | A1 * | 9/2018 | Chinnock | A61B 1/051 |

OTHER PUBLICATIONS

Krstajić, Nikola, et al., "Two-color widefield fluorescence microendoscopy enables multiplexed molecular imaging in the alveolar space of human lung tissue", *Journal of Biomedical Optics*, Apr. 30, 2016, pp. 046009-1-046009-13, vol. 21, No. 4, International Society for Optical Engineering (SPIE).

Li, David Day-Uei, et al., "Time-Domain Fluorescence Lifetime Imaging Techniques Suitable for Solid-State Imaging Sensor Arrays", *Sensors*, May 2, 2012, pp. 5650-5669, vol. 12, No. 12, retrieved from www.mdpi.com/1424-8220/12/5/5650/pdf, on Oct. 5, 2018.

Poland, Simon P., et al., "A high speed multifocal multiphoton fluorescence lifetime imaging microscope for live-cell FRET imaging", Biomedical Optics Express, Jan. 6, 2015, pp. 277-296, vol. 6, No. 2, OSA.

Poland, Simon P., et al., "Time-resolved multifocal multiphoton microscope for high speed FRET imaging in vivo", *Optics Letters*, Oct. 15, 2014, pp. 6013-6016, vol. 39, No. 20, Optical Society of America.

Rocca, Francescopaolo Mattioli Della, et al., "Real-Time Fluorescence Lifetime Actuation For Cell Sorting Using a CMOS SPAD Silicon Photomultiplier", *Optics Letters*, Feb. 15, 2016, 4 pages, vol. 41, No. 4., retrieved from https://pureportal.strath.ac.uk/files-asset/46233879/Mattioli_Della_Rocca_etal_OL_2016_Real_time_fluorescence_lifetime_actuation_for_cell_sorting_using_a_CMOS_SPAD.pdf on Oct. 5, 2018.

European Patent Office, Communication pursuant to Article 94(3) EPC received for Application No. 17718122.9, dated May 26, 2021, 4 pages, Germany.

Chen, Zhenyue, et al., "Single camera imaging system for color and near-infrared fluorescence image guided surgery", Biomed. Opt. Express, Aug. 2014, vol. 5, No. 8, pp. 2791-2797, Optical Society of America.

Dubaj, V., et al., "Optic fibre bundle contact imaging probe employing a laser scanning confocal microscope", J. Microsc., Aug. 2002, pp. 108-117, vol. 207, No. Pt 2, retrieved from the Internet at <URL: https://onlinelibrary.wiley.com/doi/ 10.1046/j.1365-2818.2002.01052.x> on Oct. 27, 2022.

Glatz, Jürgen, et al., "Concurrent video-rate color and near-infrared fluorescence laparoscopy", J. Biomed. Opt., Oct. 2013, p. 101302-1-101302-7, vol. 18, No. 10, retrieved from the Internet at <URL: https://www.spiedigital library.org/journals/Journal-of-Biomedical-Optics> on Oct. 27, 2022.

Hughes, Michael, et al., "Color reflectance fiber bundle endomicroscopy without back-reflections", J. Biomed. Opt., Mar. 2014, p. 030501-1-030501-3, vol. 19, No. 3, retrieved from the Internet at <URL: https://www.spiedigital library.org/journals/Journal-of-Biomedical-Optics> on Oct. 27, 2022.

Jabbour, Joey M. et al., "Confocal endomicroscopy: instrumentation and medical applications", Ann. Biomed. Eng., Feb. 2012, pp. 378-397, vol. 40, No. 2, Author Manuscript published Jul. 14, 2013 on NIH Public Access.

(56) References Cited

OTHER PUBLICATIONS

Koucky, Michael, et al., "Axial response of high-resolution microendoscopy in scattering media", Biomed. Opt. Express, Sep. 25, 2013, pp. 2247-2256, vol. 4, No. 10, Optical Society of America.

Krstajić, Nikola, et al., "256 ×2 SPAD line sensor for time resolved fluorescence spectroscopy", Opt. Express, Mar. 9, 2015, p. 5653-5669, vol. 23, No. 5, Optical Society of America.

Liu, Xuan, et al., "Dark-field illuminated reflectance fiber bundle endoscopic microscope", J. Biomed. Opt., Apr. 2011, pp. 046003-1-046003-7, vol. 16, No. 4, retrieved from the Internet at <URL: https://www.spiedigital library.org/journals/Journal-of-Biomedical-Optics> on Oct. 27, 2022.

Mufti, Nooman, et al., "Fiber optic microendoscopy for preclinical study of bacterial infection dynamics", Biomed. Opt. Express, May 1, 2011, pp. 1121-1134, vol. 2, No. 5, Optical Society of America.

Muldoon, Timothy J., et al., "High-resolution imaging in Barrett's Esophagus: a novel, low-cost endoscopic microscope", Gastrointest. Endosc., Oct. 2008, pp. 737-744, vol. 68, No. 4, Author Manuscript published May 13, 2010 on NIH Public Access.

Muldoon, Timothy J., et al., "Subcellular-resolution molecular imaging within living tissue by fiber microendoscopy", Opt. Express, Dec. 10, 2007, vol. 15, No. 25, p. 16413-16423, Optical Society of America.

Pierce, Mark C., et al., "Low-cost endomicroscopy in the esophagus and colon", Am. J. Gastroenterol., Sep. 2011, pp. 1722-1724, vol. 106, No. 9, Author Manuscript published Mar. 1, 2012 on NIH Public Access.

Pierce, Mark, et al., 'Video Article: High-resolution Fiber-optic Microendoscopy for in situ Cellular Imaging, J. Vis. Exp., Jan. 11, 2011, No. 47, e2306, 5 pages, published on the Internet at www.jove.com.

Roblyer, Darren, et al., "Multispectral optical imaging device for in vivo detection of oral neoplasia", J. Biomed. Opt., March/Apr. 2008, p. 024019-1-024019-11,vol. 13, No. 2, Author Manuscript published Mar. 31, 2014 on NIH Public Access.

The University of Edinburgh, "Proteus—Multiplexed Optical Molecular Sensing and Imaging—Overview", Brochure, 2015, 14 pages, UK.

Thiberville, Luc, et al., "In Vivo Imaging of the Bronchial Wall Microstructure Using Fibered Confocal Fluorescence Microscopy", Am. J. Respir. Crit. Care Med., Jan. 2007, pp. 22-31, vol. 175, No. 1, American Thoracic Society.

Venugopal, Vivek, et al., "Design and characterization of an optimized simultaneous color and near-infrared fluorescence rigid endoscopic imaging system", J. Biomed. Opt., Dec. 2013, pp. 126018-1-126018-10, vol. 18, No. 12, retrieved from the Internet at <URL: https://www.spiedigitallibrary.org/journals/Journal-of- Biomedical-Optics> on Oct. 27, 2022.

Yang, Chenying, et al., "Mitigating fluorescence spectral overlap in wide-field endoscopic imaging", J. Biomed. Opt., Aug. 2013, pp. 086012-1-086012-13, vol. 18, No. 8, retrieved from the Internet at <URL: https://www.spiedigital library.org/journals/Journal-of-Biomedical-Optics> on Oct. 27, 2022.

\* cited by examiner

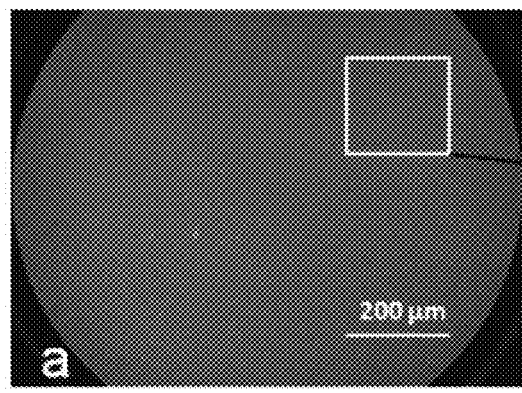
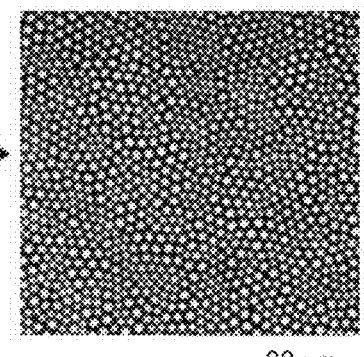
Fig. 11a        Fig. 11b
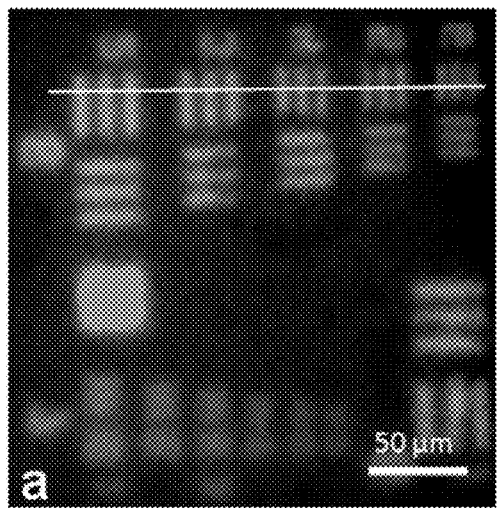
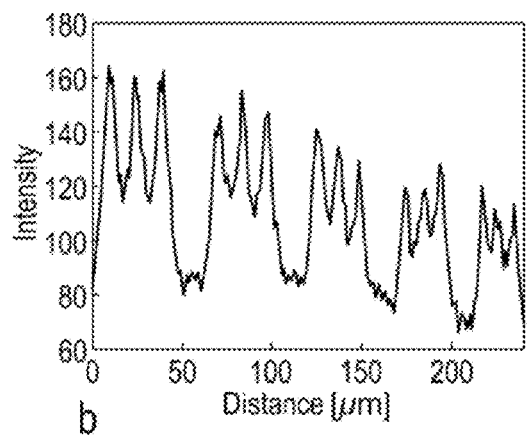
Fig. 12a        Fig. 12b

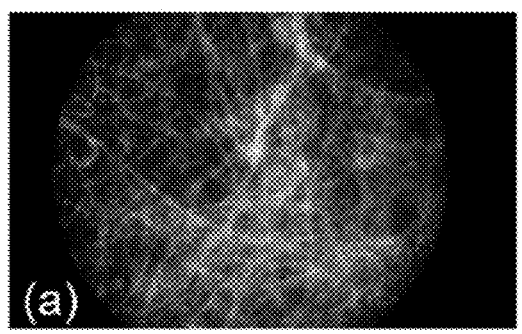
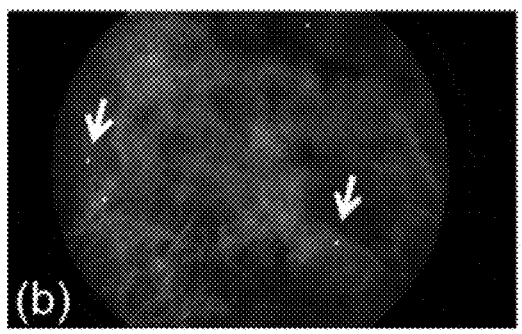
Fig. 16a　　　　　　　　Fig. 16b
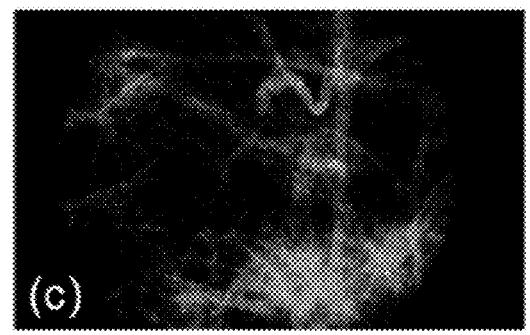
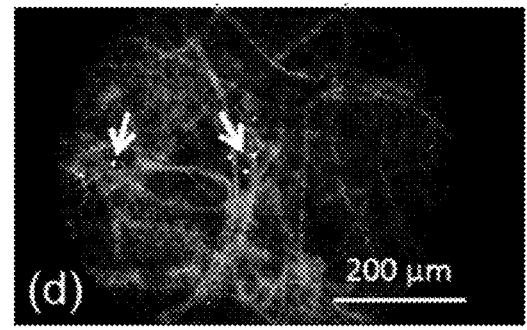
Fig. 16c　　　　　　　　Fig. 16d
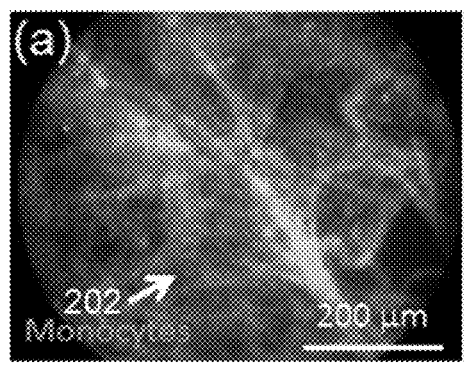
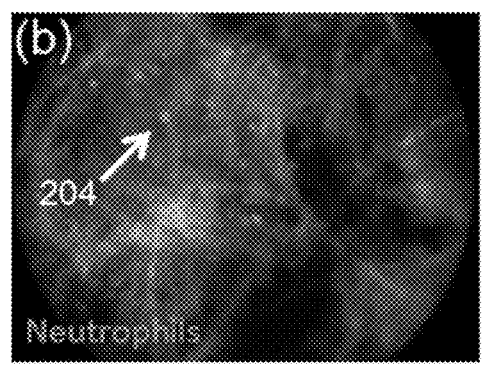
Fig. 17a　　　　　　　　Fig. 17b
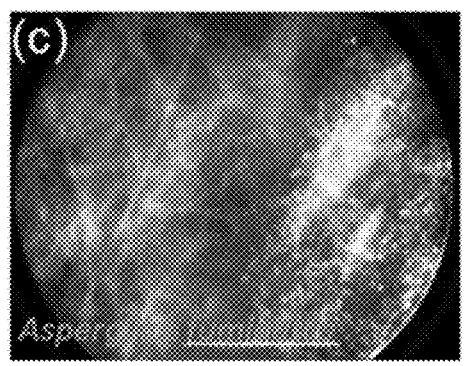
Fig. 17c

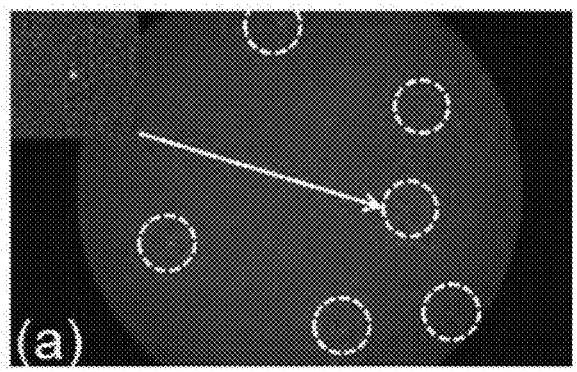
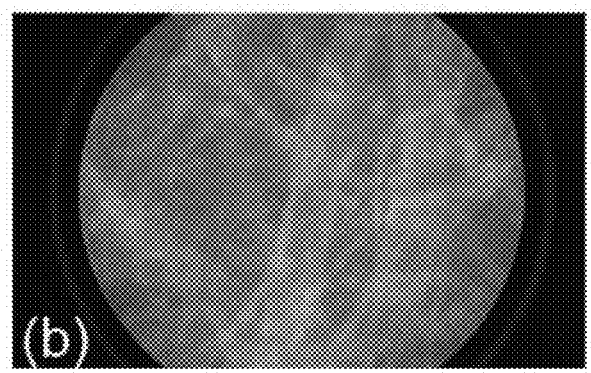
Fig. 20a                Fig. 20b
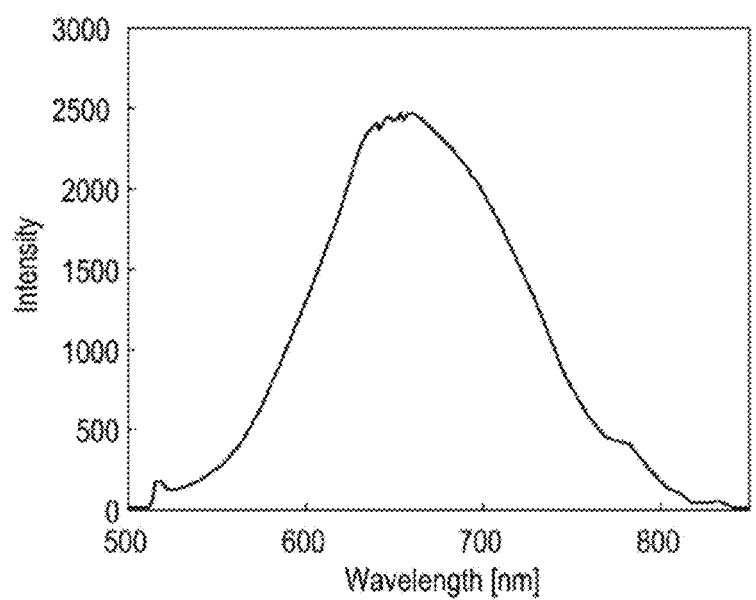
Fig. 21

ENDOSCOPIC IMAGING APPARATUS AND METHOD

CROSS REFERENCE TO RELATED APPLICATIONS

This application is a National Stage Application, filed under 35 U.S.C. § 371, of International Application No. PCT/GB2017/050975, filed Apr. 6, 2017, which claims priority to United Kingdom Application No. 1605873.7, filed Apr. 6, 2016; the contents of both of which as are hereby incorporated by reference in their entirety.

BACKGROUND

Related Field

FIELD

The present invention relates to a method and apparatus for multi-colour fluorescence and/or reflection endoscopy.

DESCRIPTION OF RELATED ART

Imaging inside the human or animal body may be performed using an endoscope. Microendoscopy may comprise the use of an endoscope to provide microscopic images. Microendoscopic imaging may be camera-based or confocal.

Confocal microendoscopy may comprise scanning a laser spot over tissue to image tissue at a particular depth. In some circumstances, confocal microendoscopy may optically section tissue at less than 20 μm to 30 μm.

Camera-based microendoscopy (which may also be referred to as widefield microendoscopy) may comprise imaging an entire field of view at once, rather than scanning. Camera-based microendoscopy may capture signals from deeper in tissue. However, in some circumstances the signals acquired in camera-based endoscopy may be so blurred that an unwanted background is created.

In the description below, the term widefield may be used to mean camera-based.

Clinical molecular imaging (MI) may cover a broad range of techniques, including fluorescence, positron emission tomography (PET), single photon emission computed tomography (SPECT) and magnetic resonance imaging (MRI).

MI aims to improve diagnosis by utilizing targeted reporters (which may be referred to as smartprobes) for specific disease targets in tissue. Smartprobes may comprise probes that may be activated (or inactivated) by interaction with a particular target. For example, the light emission properties of a smartprobe may change on interaction with a target.

Optical molecular imaging (OMI) has proven to be effective against several disease targets, for example, bacterial infection, inflammation and cancer. Several candidate smartprobes have been designed, for example smartprobes targeting neutrophil recruitment, bacterial detection and fibrogenesis.

Methods may be needed to understand disease processes in the human lung and other organs and tissues in humans and other animals. Despite decades of research and numerous models of disease, very little is known about the dynamic events that may contribute to disease pathology of the human lung, or in other human disease.

Lung inflammation and infection in critically ill ventilated patients may have a high level of mortality, often above 70%. Post mortem, pneumonia may be pathologically defined on biopsies of alveolar (distal lung) tissue infiltrated with bacteria and inflammatory cells. Obtaining information on bacterial information from a living patient may be more difficult. The most common method to determine the bacterial burden in respiratory critical care relies on the culture of bronchoalveolar lavage fluid (BALF). In bronchoalveolar lavage, fluid is introduced to a patient's lung and then collected for examination. One of the major limitations of BALF in critically ill patients may be the time taken to yield a result, which can be up to 48 hours. Another issue may be contamination by proximal airways sampling. During this intervening time before results of BALF are obtained, patients may be prescribed inappropriate therapy or deteriorate rapidly whilst awaiting a confirmatory diagnosis.

BRIEF SUMMARY

In a first aspect of the invention, there is provided an endoscopic imaging apparatus comprising: at least one light source configured to provide excitation signals to an imaging region via a common transmission path, each excitation signal having one of a plurality of different colours; a controller configured to control the at least one light source to provide the excitation signals as a repeating time-interleaved sequence that comprises at least an excitation signal of a first one of the colours and a subsequent excitation signal of a second one of the colours; and a monochrome detector configured, for each of at least some of the excitation signals, to receive at least part of a respective response signal emitted from the imaging region in response to the excitation signal and to generate image data based on the at least part of the response signal.

By using excitation signals of different colours, multiple disease targets may be imaged concurrently. More information may be obtained than with a single colour of excitation light. By providing the targets as a repeating time-interleaved sequence, image data from different colours of excitation signals may be obtained at a suitable frame rate, for example at video rate. The image data from different colours may be used to create multi-colour images.

The number of different colours may be, for example, three, four, five, or six or more. The repeating time-interleaved sequence may comprises at least the excitation signal of the first one of the colours, the subsequent excitation signal of the second one of the colours, and a further subsequent excitation signal of a third one of the colours.

The at least one light source and monochrome detector may be coupled to a proximal end of an optical fibre apparatus. The optical fibre apparatus may comprise at least part of the common transmission path. The imaging region may be positioned at or near a distal end of the optical fibre apparatus. The use of a common transmission path may reduce the complexity of the apparatus.

The apparatus may comprise a further detector and optionally a splitting device configured to receive the response signal from the imaging region, to pass said at least part of the response signal to the monochrome detector and to pass a further part of the response signal to said further detector. The use of more than one detector may allow increased information to be obtained. The splitting of the response signal may ensure that light received by the further detector corresponds to the light received at the monochrome detector.

The monochrome detector may be configured to receive the at least part of the response signal. The further detector may be configured to receive the further part of the response signal at least partly via the same optical path. The receiving of the at least part and the further part of the response signal at least partly via the same optical path may reduce the complexity of the apparatus.

The further detector may comprise a spectrometer or a time resolved detector, for example a fluorescence lifetime imaging (FLIM) detector. Each excitation signal may comprise pulsed and/or modulated light. The monochrome detector or the or a further detector may comprise a time-resolved detector configured, for each excitation signal, to perform fluorescence lifetime imaging (FLIM) of the at least part or the further part of the response signal emitted from the imaging region in response to the excitation signal. The use of FLIM may allow increased information to be obtained about the imaging region.

The time-resolved detector may comprise at least one of a time-resolved camera, a time-gated intensified CCD camera, a time-gated intensified sCMOS camera, a CMOS SPAD array, a modulatable camera.

For each excitation signal, the time-resolved detector may be configured to determine at least one fluorescence lifetime.

The apparatus may further comprise a processing resource configured, for each of at least some of the excitation signals, to distinguish between different materials in the imaging region based on the determined at least one fluorescence lifetime.

The pulsed and/or modulated light may have a pulse and/or modulation rate between 0.1 MHz and 1000 MHz, optionally between 1 MHz and 100 MHz.

The at least one light source may be configured to provide modulated light. The time-resolved detector may be configured to perform modulated FLIM.

The further detector may comprise a spectrometer. Each excitation signal may comprise pulsed and/or modulated light. The spectrometer may be configured to perform time-resolved spectroscopy.

The pulsed and/or modulated light may have a pulse and/or modulation rate between 0.1 MHz and 1000 MHz, optionally between 1 MHz and 100 MHz.

The at least one light source may comprise a plurality of light sources, each configured to provide the excitation signals of a respective one of the plurality of different colours.

The use of a plurality of light sources may allow the time-interleaved sequence to be provided in a simple and/or cost-effective manner.

The apparatus may further comprise a steering arrangement configured to direct the excitation signals to the common transmission path, wherein optionally the steering arrangement comprises at least one dichroic mirror.

The apparatus may further comprise at least one filter arranged to filter said at least part of the response signal or said further part of the response signal.

The at least one filter may comprise a variable filter, for example a filter wheel. The variable filter may provide different filtering for the response signals obtained from the excitation signals of different colours. The variable filter may be synchronised with operation of the at least one light source and/or detector or further detector to provide different filtering for the response signals obtained from the excitation signals of different colours.

The controller may be further configured to control the monochrome detector and/or further detector.

The controller may be configured to synchronise operation of at least two of the at least one light source, the detector, the further detector, the splitter, the filter, an aperture element, an aperture element in the transmission path, an aperture element in the optical path.

The or each light source may comprise at least one of an LED, a laser diode, a continuous wave LED, a continuous wave laser, a pulsed LED, a pulsed laser, a modulatable LED, a supercontinuum laser.

The excitation signals may comprise at least one of visible light, ultraviolet light, infrared light. At least one of the colours may be visible. At least one of the colours may be infrared. At least one of the colours may be ultraviolet.

Each of the excitation signals may occupies a respective time interval of between 5 ms and 500 ms, optionally between 10 ms and 100 ms, optionally between 5 ms and 50 ms, optionally less than 50 ms, optionally less than 30 ms, further optionally less than 20 ms. The length of the excitation signals may be such that images formed from image data generated from excitation signals that are adjacent in time may not require registration.

The excitation signals may be such as to produce fluorescence in at least one fluorescent material that may be present in the imaging region. The response signals may comprise fluorescent light emitted by said at least one fluorescent material.

The different colours of the excitation signals may be selected so as to produce fluorescence in different fluorescent materials.

The at least one fluorescent material may comprise at least one smartprobe, optionally at least one smartprobe that is configured to fluoresce in response to at least one of the excitation signals in the presence of a respective at least one biological target and/or in dependence on at least one environmental condition, for example pH, oxygen, glucose level, carbon dioxide.

The or each biological target may comprise at least one of: bacteria, fungus, enzymes, proteins, cells, inflammatory cells, neutrophils, macrophages, white blood cells, epithelium, endothelium.

The excitation signals may be such as to reflect from at least one material that may be present in the imaging region. The response signals may comprise reflected light reflected by said at least one material.

At least one of the plurality of excitation signals may be such as to cause autofluorescence of tissue in the imaging region.

The monochrome detector may comprise at least one of a monochrome camera, a steady-state camera, a CMOS camera, a CCD camera.

Each excitation signal may comprise continuous-wave light.

The plurality of different colours may be distributed over a wavelength range of greater than 100 nm, optionally greater than 250 nm, further optionally greater than 400 nm.

The apparatus may be configured to provide imaging in each of the plurality of different colours at a frame rate of between 0.1 fps and 400 fps.

The apparatus may be configured to provide imaging in each of the plurality of different colours at a frame rate of at least 0.1 fps, optionally at least 1 fps, further optionally at least 5 fps, further optionally at least 10 fps. The apparatus may be configured to provide imaging in each of the plurality of different colours at a frame rate of between 0.1 and 400 fps. The apparatus may provide real time information to a clinician.

The apparatus may further comprise a processing resource configured to produce at least one image data set representative of at least one image from the image data.

The at least one image may comprise a single image, for example an overlaid image, that is based on image data obtained from a plurality of the response signals obtained in response to the excitation signals of different colours.

The at least one image data set may be representative of a combination of image data from the camera and data from the at least one further detector, for example FLIM data or spectroscopy data. The combination of image data and data from the at least one further detector may allow more information to be presented to the user. The combination of image data and data from the at least one further detector may allow a greater number of biological targets to be distinguished.

The apparatus may comprise the or a processing resource configured to align image data from the camera and data from the at least one further detector.

The controller may be configured to receive user input and to control based on the user input at least one of an exposure time, a frame rate, a pulse rate, an illumination level.

The apparatus may further comprise at least one aperture element. The at least one aperture element may be configured to select a part of a field of view of the apparatus, wherein the image data is representative of an image of the selected part of the imaging region.

The optical fibre apparatus may be configured to perform contact imaging.

The optical fibre apparatus may be lensed by a gradient-index (GRIN) lens.

The optical fibre apparatus may comprise a plurality of optical fibres. A size of each optical fibre may be chosen to be larger than a size of a target object. A size of each optical fibre and cladding between the fibres may be chosen to be larger than a size of a target object. A diameter of each optical fibre may be chosen to be larger than a size of a target object. The size of each optical fibre may be larger than the size of the target object so as to cause a blinking effect as the target object moves relative to the optical fibres. A blinking effect may be caused by the object's size being smaller than a cladding of each optical fibre. When the target object moves relative to the plurality of optical fibres, it may move between fibre and cladding, therefore changing in visibility. The target object may comprise at least one of: bacteria, fungus, enzymes, proteins, cells, inflammatory cells, neutrophils, macrophages, white blood cells, epithelium, endothelium. The optical fibres may be made of and/or comprise any suitable material for example any suitable glass or plastic material.

The distal end of the optical fibre apparatus may be configured for attachment of a droplet. The droplet may comprise at least one of tissue, fluorescent material. The fluorescent material may comprise at least one probe, optionally at least one smartprobe. Imaging and/or spectroscopy may be performed on the droplet. The use of a droplet may provide imaging and/or spectroscopy that may be substantially free of tissue background.

The apparatus may further comprise an optical element positioned in the common transmission path. The optical element may be configured or configurable to reflect at least part of each of the excitation signals towards the imaging region, and to transmit at least part of each of the response signals to the detector.

The optical element may be configured to act as a dichroic mirror for a first range of wavelengths comprising at least one of the plurality of colours, and to act as a beamsplitter for a second, different range of wavelengths comprising at least one other of the plurality of colours.

The optical element may be configured to reflect substantially all incident light in the first range of wavelengths. The optical element may be configured to reflect a majority of incident light in the first range of wavelengths. The optical element may be configured, for incident light in the first range of wavelengths, to reflect more than 70% of the incident light, optionally more than 80%, further optionally more than 90%, further optionally more than 95%. The optical element may be configured, for incident light in the first range of wavelengths, to transmit less than 20% of the incident light, optionally less than 10%, further optionally less than 5%.

It may not be possible to manufacture the optical element so that all of the incident light in the first range of wavelengths is reflected. However, the amount of incident light in the first range of wavelengths that is transmitted may be minimal or negligible.

The optical element may be configured or configurable to transmit substantially all incident light in a further range of wavelengths corresponding to fluorescence produced in response to light in the first range of wavelengths. The optical element may be configured, for incident light in the further range of wavelengths, to transmit more than 70% of the incident light, optionally more than 80%, further optionally more than 90%, further optionally more than 95%.

The optical element may be configured or configurable to divide incident light in the second range of wavelengths into two portions by transmitting a first portion of the light and reflecting a second portion of the light. A ratio of the portions may be between 80/20 and 20/80, optionally between 60/40 and 40/60, further optionally between 55/45 and 45/55.

The optical element may be configured to act as a dichroic mirror for a first range of wavelengths comprising at least one of the plurality of colours, and to act as a beamsplitter for a second, different range of wavelengths comprising at least one other of the plurality of colours for light that is incident upon the dichroic at an angle between 30% and 60%, optionally between 40% and 50%.

The optical element may be a single, integrated element. The optical element may comprise a thin film interference filter.

The apparatus may be configured to perform fluorescence imaging using excitation signals having the first at least one of the plurality of colours, and to perform reflection imaging using excitation signals having the second at least one of the plurality of colours.

In a further aspect of the invention, there is provided an endoscopic imaging apparatus comprising: at least one light source configured to provide excitation signals to an imaging region via a common transmission path, each excitation signal having one of a plurality of different colours; a controller configured to control the at least one light source to provide the excitation signals; a detector configured, for each of at least some of the excitation signals, to receive at least part of a respective response signal emitted from the imaging region in response to the excitation signal and to generate image data based on the at least part of the response signal; and an optical element positioned in the common transmission path and configured to reflect at least part of each of the excitation signals towards the imaging region, and to transmit at least part of each of the response signals to the detector; wherein the optical element is configured to act as a dichroic mirror for a first range of wavelengths comprising at least one of the plurality of colours, and to act as a beamsplitter for a second range of wavelengths comprising at least one other of the plurality of colours.

In a further aspect of the invention, there is provided an integrated, integral or unitary optical element as claimed or described herein. The optical element may be a single optical element that is configured to act as a dichroic mirror for a first range of wavelengths comprising at least one of the plurality of colours, and to act as a beamsplitter for a second range of wavelengths comprising at least one other of the plurality of colours.

In a further aspect of the invention there is provided endoscopic imaging method comprising: providing by at least one light source excitation signals to an imaging region via a common transmission path, each excitation signal having one of a plurality of different colours; controlling by a controller the at least one light source to provide the excitation signals as a repeating time-interleaved sequence that comprises at least an excitation signal of a first one of the colours and a subsequent excitation signal of a second one of the colours; and, for each of at least some of the excitation signals, receiving by a monochrome detector at least part of a respective response signal emitted from the imaging region in response to the excitation signal and generating image data based on the at least part of the response signal.

Features in one aspect may be provided as features in any other aspect as appropriate. For example, features of a method may be provided as features of an apparatus and vice versa. Any feature or features in one aspect may be provided in combination with any suitable feature or features in any other aspect.

BRIEF DESCRIPTION OF THE FIGURES

Embodiments of the invention are now described, by way of non-limiting example, and are illustrated in the following figures, in which:—

FIGS. 11a and 11b are images of a fibre bundle as acquired by a camera;

FIG. 12a is an image of a USAF 1951 test target illuminated with an even fluorescent signal;

FIG. 12b is a line profile across group 6 elements of the USAF 1951 test target of FIG. 12a;

FIG. 16a is a 20 fps image with 0.3% Inspeck microspheres;

FIG. 16b is a 20 fps image with 3% Inspeck microspheres;

FIG. 16c is a 200 fps image with 0.3% Inspeck microspheres;

FIG. 16d is a 200 fps image with 3% Inspeck microspheres;

FIGS. 17a, 17b and 17c are images of targets in ex vivo lung tissue including monocytes, neutrophils and fungus respectively;

FIGS. 19a, 19b and 19c are a sequence of three images demonstrating one mechanism of blinking of bacteria moving between fibre cores;

FIG. 20a is an image of 0.3% Inspeck microspheres visible against background at 1 mW 470 nm LED illumination;

FIG. 20b is an image of 0.3% Inspeck microspheres not visible against background at 2.4 mW 470 nm LED illumination;

FIG. 21 is a plot of a fibre bundle fluorescence spectrum;

DETAILED DESCRIPTION OF VARIOUS EMBODIMENTS

Figure 1:
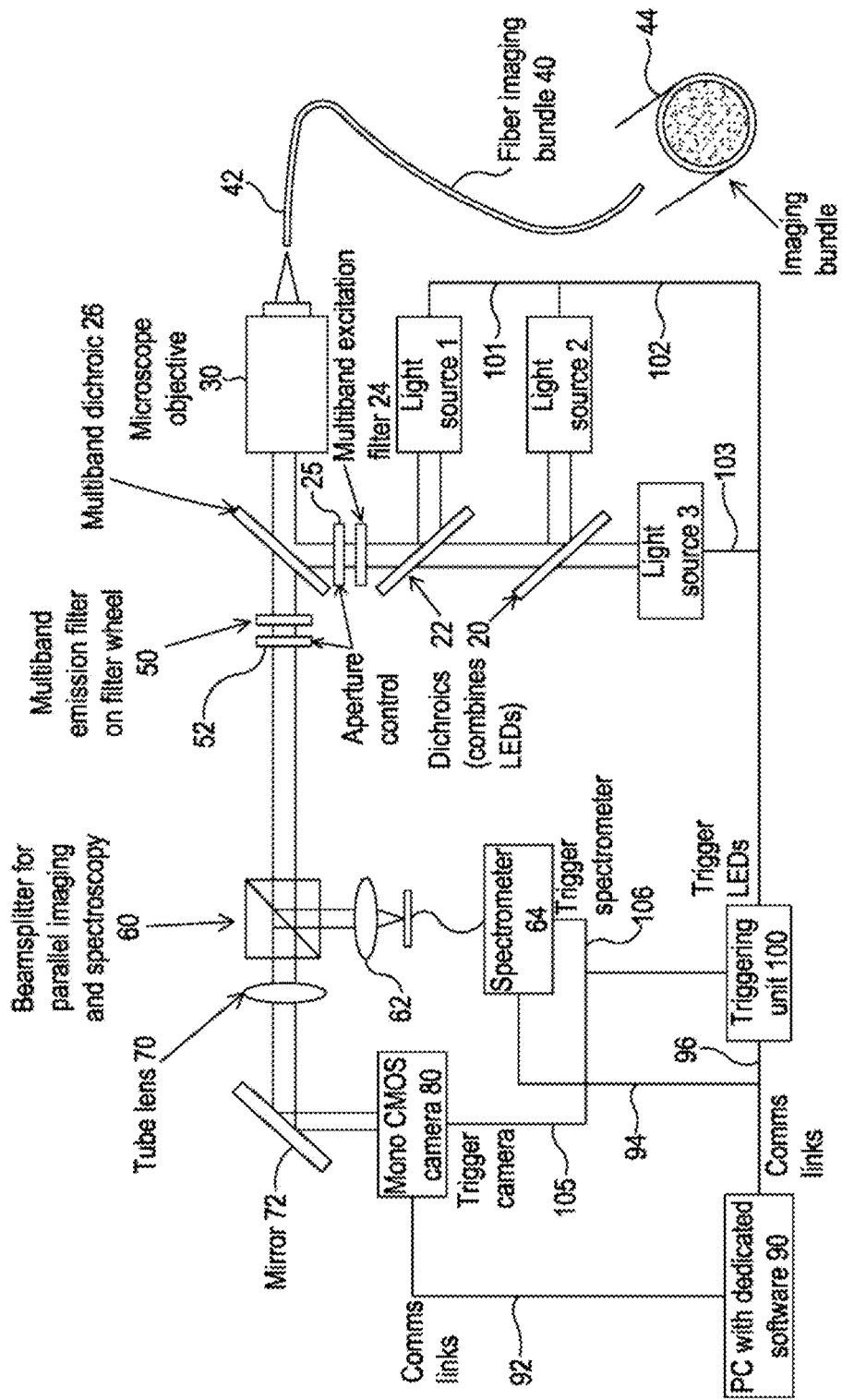
FIG. 1 is a schematic illustration of a three-color fluorescence system in accordance with an embodiment.

FIG. 1 is a schematic illustration of a camera-based (widefield) fluorescence microendoscopy system in accordance with an embodiment. The system of FIG. 1 is based on sequential pulsing of light sources. The system of FIG. 1 comprises an optical device using a fast CMOS camera and three triggered LEDs of differing wavelengths to generate multi-colour fluorescence. The system of FIG. 1 may provide a low-cost and simple route to multi-colour fluorescence endoscopy via camera-based (widefield) detection.

The system of FIG. 1 is configured to provide spectroscopy in addition to multi-colour fluorescence imaging of tissue. In other embodiments, the spectroscopy capability of the system may be omitted.

In the present embodiment, the system of FIG. 1 is used for imaging combined physiology (e.g. tissue structure) and pathology (presence of bacteria and/or neutrophils) in the distal lung via a fibre optic bundle. The system of FIG. 1 may be used to image and/or detect a number of different disease targets concurrently, for example to image and/or detect one or more of bacteria, neutrophils, macrophages or fungus. The use of multiple colours, and the combination of multi-colour and spectroscopy, may allow the different disease targets to be distinguished.

Further embodiments may be configured for use in imaging different anatomical regions. Further embodiments may be configured for imaging and/or detecting different disease targets.

The system of FIG. 1 comprises an optical instrument, a fibre bundle 40 and a PC 90. The optical instrument comprises all the components of the system of FIG. 1 excepting the fibre bundle 40 and PC 90, and is housed in a single enclosure. In other embodiments, the components of FIG. 1 may be arranged in any suitable manner as one or more apparatuses, and may be housed in one or more enclosures as appropriate. Each of the components of FIG. 1 may be replaced by a plurality of components providing the functionality of the single component, or a plurality of components of FIG. 1 may be replaced by a single component having the functionality of the plurality of components. In some embodiments, one or more of the components shown in FIG. 1 is omitted, or additional components are added. For example, in some embodiments, a unit is provided that includes light sources, control electronics and in some cases spectrometer or FLIM detector, and a separate unit is provided that includes the monochrome camera. In some embodiments, a portable unit is provided that includes optical components and the monochrome camera, and further unit is provided that includes the light sources, triggering unit and spectrometer. The portable unit may include a display. The provision of a display in the portable unit may in some circumstances improve usability for clinicians. Any other suitable combinations of units including different combinations of the components may be provided in alternative embodiments. The use of two or more units may provide modularity.

The system of FIG. 1 comprises three light sources 1, 2, 3 of different colours. Light sources of different colours may be light sources that are configured to emit light of different frequencies, for example light having different ranges or bands of frequencies. Each light source 1, 2, 3 may emit light of a different frequency range or band. The ranges or bands may be at least partially overlapping. The light may be light that is visible to the human eye or not visible to the human eye and may be in any suitable part of the electromagnetic spectrum. Each light source 1, 2, 3 may emit light having a different frequency spectrum. Each of the different colours may comprise visible, infrared or ultraviolet light.

In the present embodiment, the light sources are a near-IR LED 3 (780 nm, 3 mW power), a red LED 2 (625 nm, 3 mW power) and a blue LED 1 (470 nm, 2 mW power). In other embodiments, any suitable light sources may be used. For example, the light sources may comprise LEDs or laser diodes. The light sources may be steady state, for example continuous wave (CW) LED or CW laser. The light sources may be pulsed or modulatable. For example, the light sources may comprise pulsed LED, pulsed laser, or modulatable LED light sources.

Any suitable number of light sources of different colours may be used, for example three, four, five, or six or more light sources. In some embodiments, using a greater number of light sources of different colours may allow a greater number of disease targets to be imaged and/or detected.

In some embodiments, a single light source may be used to provide light of different colours at different times. For example, light of different colours may be provided by a single supercontinuum laser with a suitably fast filter in front, for example an acousto-optic filter.

The system of FIG. 1 further comprises a first dichroic mirror 20, second dichroic mirror 22, multi-band excitation filter 24, aperture control 25 and multi-band dichroic mirror 26. The first dichroic mirror 20 is configured to combine light from light source 3 and light source 2. The second dichroic mirror 22 is configured to combine the output of the first dichroic mirror 20 with light from light source 1. Light from the three light sources 1, 2, 3 is thereby combined and collimated into a single transmission path.

Figure 2A:
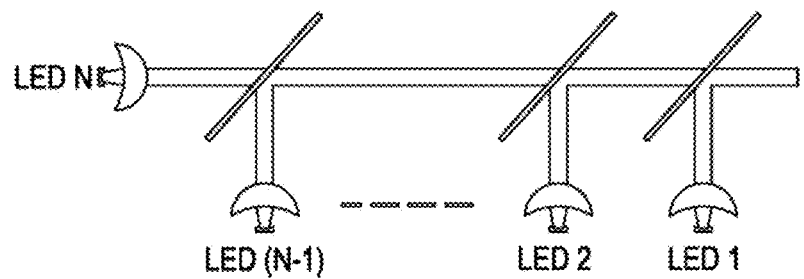
FIG. 2a is a schematic illustration of a combination of four or more LEDs.

Although the present embodiment uses three LEDs, in other embodiments a greater number of LEDs may be used. FIG. 2a shows how many (N>3) LEDs can be combined into a single path. Each LED is collimated by a condenser lens and a suitable dichroic reflects this collimated beam. Constraints on each dichroic include that each dichroic needs to reflect its respective LED and to pass all LEDs further up the chain up to LED N. For example, the dichroic for LED 2 of FIG. 2a needs to reflect light from LED 2 and to transmit light from LEDs of higher number up to LED N.

The collimated beam of LEDs goes towards the multiband filter 22 and multiband dichroic 26. In some embodiments, each LED need not have a separate band. Several LEDs can serve the same band. For example, the configuration of the present embodiment has the blue band to be 430 nm to 500 nm. Three standard LED wavelengths in this band are 455 nm, 470 nm and 490 nm LED, each of which can be used for a potentially broad blue LED illumination or sequenced excitation of fluorophores with absorption spectra matching of the LEDs involved. This may create multiple green fluorescence images which may be suitably merged by applying standard spectral unmixing techniques.

The multi-band excitation filter 24 and aperture control 25 are positioned such that light exiting the second dichroic mirror 22 is passed through the multi-band excitation filter 24 and then through aperture control 25 before being reflected from multi-band dichroic mirror 26.

The system of FIG. 1 further comprises a microscope objective 30 and the fibre imaging bundle 40. The fibre bundle 40 has a proximal end 42 and a distal end 44. The microscope objective 30 is coupled to the proximal end 42 of the fibre bundle 40. Light from all three light sources 1, 2, 3 follows a single optical path through the microscope objective 30 and into the fibre bundle 40. The multi-band dichroic mirror 26 is positioned to direct the light reflected from multi-band dichroic mirror 26 into the microscope objective 30 and thereby into the fibre bundle 40.

In the present embodiment, the microscope objective 30 is a glass microscope objective. The microscope objective 30 may be any suitable infinity corrected refractive objective, for example, Thorlabs RMS10x. In some embodiments, a reflector microscope may be used instead of a glass microscope. Using a reflector microscope may result in a less achromatic system. In the system of FIG. 1, which uses a lens in the microscope objective, the different colours of light may not focus in exactly the same place. If a convex mirror were used instead of the lens, different colours of light may reflect in the same way. The microscope objective 30 may be any suitable reflective objective, for example Edmund Optics #59-888. Reflective objectives may be inherently achromatic due to broadband mirrors in the design, which may allow better multi-colour imaging performance from UV to IR.

In use, the distal end 44 of the fibre bundle 40 is positioned inside the body of a human or animal subject, for example inside the lung of a patient. Any suitable method of deploying the fibre bundle 40 in the body of the subject may be used.

In the present embodiment, the system of FIG. 1 is used in conjunction with flexible bronchoscopy for imaging of the distal lung. The fibre bundle 40 is selected to be narrower than the working channel of a bronchoscope. The diameter of the working channel available on a modern flexible bronchoscope may range from, for example, 1 mm to 3 mm.

The diameter of the fibre bundle may be selected to be, for example, less than 1 mm or less than 2 mm.

A modern flexible bronchoscope may be, for example, 4 mm to 6 mm in diameter. In some circumstances, flexible bronchoscopy may be able to access trachea, bronchi and bronchioles but may not itself be able to access the distal lung.

The narrow fibre bundle 40 is inserted through the working channel of the bronchoscope and deployed from the working channel into the distal lung. Because the fibre bundle 40 is narrower than the bronchoscope, it may be able to extend further into the distal lung. A microendoscope probe such as fibre bundle 40 that is narrower than a bronchoscope may be used to enable safe access to the distal lung (alveolar regions) through a transbronchial pass.

Bronchoscopic interventions may last up to 60 minutes (for example, 20 to 30 minutes) and navigation may be guided by prior x-ray radiographs or computed tomography (CT) scans. Automated navigation software may be deployed.

In use, when the distal end of the fibre bundle 40 is positioned inside the body of the subject, light from the light sources 1, 2, 3 is transmitted down the fibre bundle 40 to its distal end 44. Light from all three sources 1, 2, 3 follows a common optical path. However, light from different light sources is transmitted at different times, as described below with reference to FIG. 2b.

Light from the light sources 1, 2, 3 illuminates tissue in an imaging region. The imaging region is a region that is positioned at or near the distal end of the fibre bundle 40, and may be in contact with the distal end 44 of the fibre bundle 40. For example, the imaging region may extend over an area corresponding to a field of view of the fibre bundle 40, and may extend into the tissue by a depth of, for example, 100 μm or 200 μm. The extent of the imaging region may be different for different wavelengths of light. In some embodiments, molecules of one or more probes (for example, one or more smartprobes) may be present in the imaging region, as is described in more detail below.

In the present embodiment, the fibre imaging bundle 40 is an Alveoflex™ endoscope from Mauna Kea Technologies, Paris, France. The fibre imaging bundle 40 comprises 25000 cores, and has a 600 μm diameter (field of view) and 0 μm working distance. Zero working distance entails touching the tissue that is to be imaged. Therefore, the imaging region includes tissue that is in contact with the endoscope. Zero working distance may be relevant to capturing a large amount of emitted fluorescence. In other embodiments, any suitable fibre bundle may be used, for example a fibre bundle having any suitable number of cores.

Light from each of the light sources 1, 2, 3 excites tissue and/or smartprobes in the imaging region. Light from different ones of the light sources may excite different materials, for example different smartprobes. In response to excitation by the light from each of the light sources 1, 2, 3, fluorescent light is emitted from the imaging region. The fluorescent light is collected by the distal end 44 of the fibre bundle 40 and is transmitted to the proximal end 42 of the fibre bundle 40.

In other embodiments, the light that is collected by the fibre bundle 40 may be reflected light, i.e. light at the wavelength of interrogation. For example, reflective imaging may be performed with a lensed fibre bundle 40, for example a fibre bundle 40 that is lensed by a gradient-index (GRIN) lens. In some embodiments, the fibre bundle is used for dark field imaging, which may be reflective.

The system of FIG. 1 further comprises a multi-band emission filter 50 that is positioned on a filter wheel (not shown), and a further aperture control 52. Fluorescent light that is returned from the distal end 44 of the fibre bundle 40 passes through the microscope objective 30, through the multi-band dichroic mirror 26, through the multi-band emission filter 50, and then through the further aperture control 52.

In the present embodiment, the filter wheel is manual. In other embodiments, the filter wheel may be motor controlled. In some embodiments, control of the filter wheel may be used as an optimisation step. For example, a green only filter may be chosen from the filter wheel to suppress red fluorescence if only green fluorescence is of interest.

In further embodiments, any appropriate component may be motor controlled, for example beamsplitter 60 (described below). In some embodiments, any appropriate component may be automatically controlled, for example any appropriate filter wheel, beamsplitter, dichroic, iris or aperture.

The aperture controls 25, 52 may be used to select a part of the field of view of the fibre bundle 40. Imaging and/or spectroscopy may then be performed on the selected part of the field of view, which may be a portion of the total available field of view. In further embodiments, the aperture controls 25, 52 may be omitted from the system.

The system of FIG. 1 further comprises a beamsplitter 60, a lens 62 and a spectrometer 64. The beamsplitter 60 receives the fluorescent light that has passed through the multi-band emission filter 50 and aperture control 52. In the present embodiment, the beamsplitter 60 is a 90:10 beamsplitter and is configured to send 10% of the light that it receives to the spectrometer 64 via the lens 62. In other embodiments, the beamsplitter 60 may send a different proportion of the light to the spectrometer 64. For example, the beamsplitter 60 may be a 50:50 beamsplitter. In further embodiments, no spectrometer 64 may be present. In some such embodiments, beamsplitter 60 and lens 62 may be omitted.

The system of FIG. 1 further comprises a tube lens 70, mirror 72 and detector 80. In the present embodiment, the detector 80 is a monochrome CMOS (complementary metal-oxide semiconductor) camera 80. The beamsplitter 60 is configured to send 90% of the fluorescent light that it receives through tube lens 70. Fluorescent light that has passed through the tube lens 70 reflects from mirror 72 into the monochrome CMOS camera 80.

In other embodiments, any suitable detector 80 may be used. The detector 80 may be any suitable camera, for example any suitable CMOS or CCD camera. The detector 80 may be any suitable monochrome camera. A monochrome camera may be a camera in which substantially all sensor elements of the camera are configured to respond to or acquire light across the whole range of frequencies sensed by the camera.

Substantially all of the sensor element may have the same sensitivity profile. (In contrast, a colour camera may be one in which different sensor elements are configured to respond to or acquire different colours, for example by use of a Bayer filter.) The monochrome camera may be configured to accept a range of wavelengths of light that includes wavelengths of fluorescent light emitted by the imaging region in response to illumination by each one of the light sources 1, 2, 3.

The system of FIG. 1 further comprises a computing apparatus 90 and a triggering unit 100. In the present embodiment, the computing apparatus 90 comprises a PC having dedicated software. In other embodiments, any suitable computing apparatus 90 may be used.

In other embodiments, a single apparatus may provide the functionality of computing apparatus 90 and of triggering unit 100. In further embodiments, the functionality of the computing apparatus 90 and/or triggering unit 100 may be distributed between a plurality of apparatuses.

In the present embodiment, computing apparatus 90 is connected to the monochrome camera 80, spectrometer 64 and triggering unit 100. PC 90 is connected to the monochrome CMOS camera 80 via a communications link 92, which in the present embodiment is a USB3 link. In further embodiments, the communication link 92 may comprise any fast link, for example USB3, gigabit Ethernet, FireWire or CameraLink. PC 90 is connected to the spectrometer 94 via a communications link 94, which in the present embodiment is a USB2 link. PC 90 is connected to the triggering unit 100 via a communications link 96, which in the present embodiment is a USB2 link. Each of communications links 94, 96 may comprise any suitable link. Each of the monochrome camera 80, spectrometer 64 and triggering unit 100 may receive information from and/or send information to the PC 90 via its respective link.

Triggering unit 100 is connected to light sources 1, 2, 3 by communications links 101, 102 and 103 respectively. Triggering unit 100 is connected to the monochrome CMOS camera 80 by communications link 105 and is connected to the spectrometer 64 by communications link 106. Communications links 101, 102, 103, 105, 106 may each comprise any suitable link, for example USB3, gigabit Ethernet or FireWire.

The triggering unit 100 may be described as a controller. The triggering unit 100 is configured to control timing of the light sources 1, 2, 3, monochrome camera 80 and spectrometer 64, such that the monochrome camera 80 and spectrometer 64 are synchronised with the light sources 1, 2, 3. In other embodiments, the triggering unit 100 is configured to control timing of a greater number of light sources.

Figure 2B:
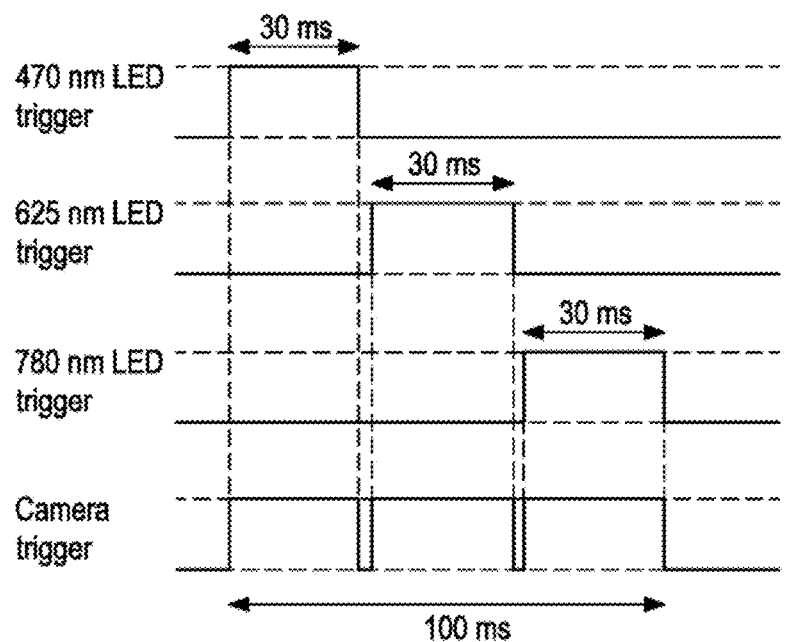
FIG. 2b is a plot showing pulsing of LEDs.

The triggering unit 100 switches the light sources 1, 2, 3 on and off in pre-defined sequences. The triggering of the light sources 1, 2, 3 by the triggering unit 100 in the present embodiment is represented in the diagram of FIG. 2b.

The triggering unit 100 turns on light source 1 (blue LED, 470 nm) for a time interval of 30 ms. The light emitted by the blue LED 1 during this 30 ms time interval may be described as a 30 ms pulse. The light emitted by the blue LED 1 during this 30 ms time interval may be described as an excitation signal having a duration of 30 ms. The excitation signal is transmitted to the imaging region as described above with reference to FIG. 1. The excitation signal excites fluorescent material in the imaging region. In response to the excitation signal, the fluorescent material emits a response signal comprising fluorescent light.

The triggering unit 100 triggers the monochrome camera 80 to acquire data for a 30 ms time interval that is synchronised with the time interval of the excitation signal. The monochrome camera 80 receives part of the response signal emitted by the imaging region in response to the excitation signal. (In the present embodiment, the monochrome camera 80 may receive 90% of the fluorescent light received by the beamsplitter.)

The monochrome camera 80 uses the part of the response signal that it received to obtain a first set of image data. The first set of image data is representative of an image of the imaging region when illuminated by the 30 ms excitation signal from the blue LED 1. The set of image data may comprise an intensity value for each pixel of the camera 80. The intensity values may correspond to the amount of fluorescent light received by each pixel.

Although not shown in FIG. 2b, the triggering unit 100 also triggers the spectrometer 64 to acquire data for a synchronised 30 ms time interval. The spectrometer 64 receives part of the response signal emitted by the imaging region in response to the excitation signal. (In the present embodiment, the spectrometer 64 may receive 10% of the fluorescent light received by the beamsplitter.) The spectrometer 64 obtains a spectrum of the response signal, i.e. a spectrum of the fluorescent light emitted by the imaging region in response to the excitation signal.

The synchronisation of the camera 80, spectrometer 64 and light source 3 by the triggering unit 100 allows the response signal received within this 30 ms period in response to the excitation from light source 3 to be associated with light source 3. In further embodiments, the triggering unit 100 may also synchronise operation of the filter 50. The triggering unit 100 may synchronise operation of the beamsplitter 60. The triggering unit 100 may synchronise operation of the aperture element 25 in the excitation path and/or aperture element 52 in the emission path.

There follows a short interval (for example, 5 ms) in which the triggering unit 100 turns off all the light sources 1, 2, 3. In this interval, the camera 80 and spectrometer 64 may also be turned off and/or the camera 80 and spectrometer 64 may not record any data received. In some embodiments, the camera 80 and spectrometer 64 record data continuously, but data within the short interval between excitation signals is not used in subsequent processing.

The triggering unit 100 then turns on light source 2 (red LED, 625 nm) for a time interval of 30 ms to provide a second excitation signal. The second excitation signal excites fluorescent material in the imaging region (which may be different fluorescent material by that excited by the first, blue excitation signal). The triggering unit 100 triggers the camera 80 and spectrometer 64 to acquire data for a time interval synchronised with the 30 ms period for which light source 2 is turned on. Each of the camera 80 and spectrometer 64 receives a part of the response signal that is emitted by fluorescent material in the imaging region in response to the second excitation signal. The camera 80 obtains a second set of image data. The spectrometer 64 obtains a second spectrum.

The triggering unit 100 turns off all the light sources 1, 2, 3 for another short interval (for example, 5 ms) in which the camera 80 and spectrometer 64 may not record data.

The triggering unit 100 then turns on light source 3 (near-IR LED, 780 nm) for a time interval of 30 ms to provide a third excitation signal. The third excitation signal excites fluorescent material in the imaging region (which may be different fluorescent material by that excited by the first and/or second excitation signal). The triggering unit 100 triggers the camera 80 and spectrometer 64 to acquire data for a time interval synchronised with the 30 ms period for which light source 2 is turned on. Each of the camera 80 and spectrometer 64 receives a part of the response signal that is emitted by fluorescent material in the imaging region in response to the third excitation signal.

The camera 80 obtains a third set of image data. The spectrometer 64 obtains a third spectrum.

The camera 80 sends the first, second and third sets of image data to the PC 90. The PC 90 uses the first, second and third sets of image data to generate and display to a user a three-colour image in which images for each of the three colours of light source are overlaid.

In other embodiments, the PC 90, camera 80 or a further processing device may store the first, second and third sets of image data in memory. The PC 90, camera 80 or further processing device may use the first, second and third sets of image data to generate and optionally to display to a user respective first, second and third images corresponding to the first, second and third excitation signals. The PC 90, camera 80 or further processing device may use the first, second and third sets of image data to generate and optionally display to a user a three-colour image in which images for each of the three colours are overlaid.

The 100 ms three-colour time-interleaved sequence of excitation signals shown in FIG. 2*b* is repeated over a period of time, for example a period of some seconds or minutes. Although FIG. 2*b* only shows the triggering sequence for the light sources 1, 2, 3 and camera 80, the spectrometer 64 is also triggered at the same times as the camera 80.

The light sources are triggered to provide a repeating sequence of excitation signals (in this case, 1, 2, 3, 1, 2, 3 etc.) in which excitation signals from each of the light sources are time-interleaved. Each excitation signal comprises a pulse of light from a respective one of the light sources. Light from each of the light sources is provided to the imaging region in alternating time intervals.

The triggering of the monochrome camera 80 and spectrometer 64 allows each interval in a light source ON/OFF sequence to be associated to a defined fluorescence channel.

For each repetition of the three-colour sequence of FIG. 2*b*, the PC 90 generates and displays a respective three-colour image from image data obtained in response to the first, second and third excitation signals for that repetition. The PC 90 obtains the three-colour image by overlaying images for each of the three colours. The PC 90 generates and displays three-colour images at a frame rate of 10 frames per second (fps). In other embodiments, an image may be generated for each of the individual excitation signals, the images alternating between blue, red and near-IR illumination. For example, 30 images may be obtained per second, comprising 10 images of the imaging region under blue illumination, 10 under red illumination and 10 under near-IR illumination.

In the present embodiment, it has been found that the speed at which the LEDs are triggered is fast enough that each overlaid image of the three different colours is well aligned. In other embodiments, any suitable method may be used to overlay images in different colours.

For each of the excitation signals, the spectrometer 64 and/or PC 90 may be used to analyse the spectra obtained by the spectrometer 64 from the corresponding response signal. The spectra received by the spectrometer 64 may be used to distinguish different materials in the imaging region, for example to distinguish different materials that produce fluorescent light of similar wavelengths.

The depth of field of the imaging region from which fluorescent light is returned to the camera 80 and spectrometer 64 may be, for example, 100 µm or 200 µm. The depth of field of a camera-based system may allow spectra to be obtained from a large volume simultaneously.

Figure 4:
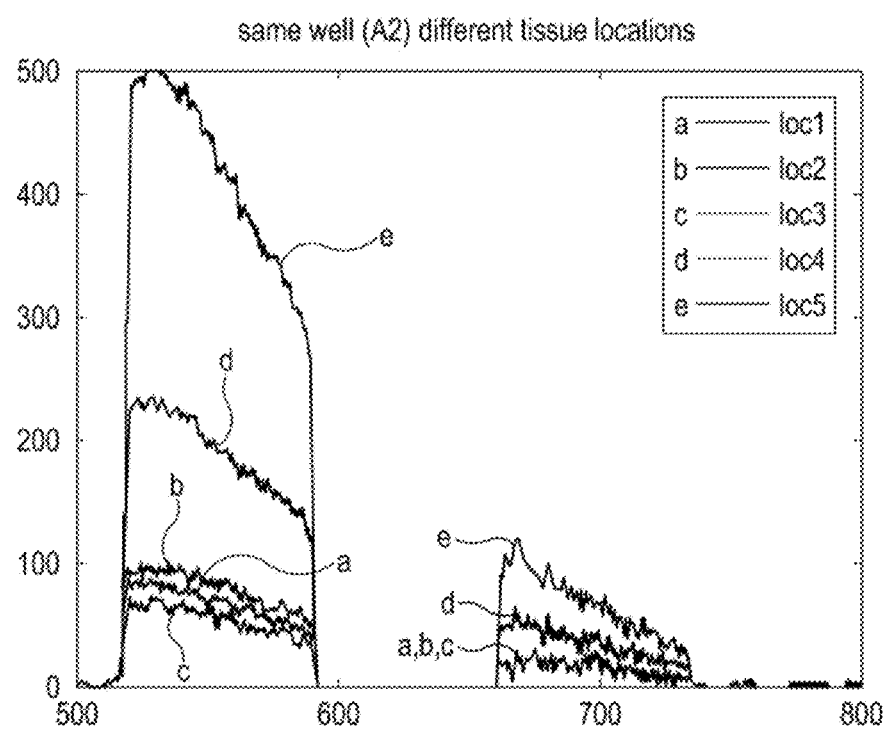
FIG. 4 is a plot of a plurality of spectra from lung tissue.

FIG. 4 demonstrates a capability of the system of FIG. 1 to acquire spectra from lung tissue. 5 spectra were acquired from 5 locations of a well plate, demonstrating a variability of tissue spectroscopy. FIG. 4 demonstrates that many spectra may be taken from many locations.

The system of FIG. 1 is configured to obtain images of tissue in the imaging region at the distal end 44 of the fibre bundle 40, and to perform spectroscopy on the tissue in the imaging region. In the present embodiment, the tissue to be imaged is tissue of the distal lung. In other embodiments, any appropriate human or animal tissue may be imaged. By using different colours of light, and by combining imaging and spectroscopy, multiple different disease targets may be distinguished.

In some embodiments, including the present embodiment, molecules of one or more probes are introduced into the imaging region. Each of the probes is configured to fluoresce under illumination by one or more of the light sources. One or more of the probes may be a smartprobe that is configured to be activated (or inactivated) by interaction with a particular target, for example activation with a particular disease target.

In the present embodiment, molecules of two different smartprobes are introduced into the imaging region that is to be imaged by the system of FIG. 1. A first smartprobe is a smartprobe that is used to label macrophages. A frequency of the NIR light source 3 is configured to excite molecules of the first smartprobe. Images obtained using the NIR light source 3 may therefore be used to image macrophages in the imaging region, for example to determine whether macrophages are present in the imaging region.

A second smartprobe in the present embodiment is a smartprobe that is used to label bacterial colonies. A frequency of the red light source 2 is configured to excite molecules of the second smartprobe. Images obtained using the NIR light source 3 may therefore be used to image bacterial colonies in the imaging region, for example to determine whether bacterial colonies are present in the imaging region.

A frequency of the blue light source 1 is configured to excite autofluorescence of lung tissue. Lung or any animal tissue may fluoresce due to the presence of compounds such as elastin, collagen and/or other proteins. Autofluorescence may comprise collective fluorescence of many proteins, for example of dozens of proteins. Peak autofluorescence may occur when excited in UV, but autofluorescence may also be excited when sending 470 nm LED light into tissue.

In the present embodiment, macrophages were pre-labelled with IRDye800CW and bacterial colonies with PKH red (CellClaret). In other embodiments, different probes may be used and/or the probes may be used to label different disease targets. In the present embodiment, the system is tested for detection of objects in different colours. In other embodiments, if smartprobes were used that labelled the same objects with the same intensity, the objects would be visible.

Custom smartprobes may be deployed. Each of the smartprobes may be configured to be used in imaging a respective pathology, for example in imaging bacteria or neutrophils. Some smartprobes may indicate the activity of enzymes. Some smartprobes may provide information about inflammation. Some smartprobes may distinguish cancerous tissue from benign tissue.

Smartprobes may provide information about chemical activity. In such cases, the system may return a signal rather than an image for that smartprobe. The depth of field of the camera-based system may allow a larger signal to be obtained than if a lower depth of field were to be used. In some circumstances, probes may diffuse over a large area.

In the present embodiment, each light source is turned on for 30 ms then turned off again. The use of periodic illumination by each light source (for example, turning on each light source for only 30 ms of each 100 ms period) may prevent or reduce quenching of fluorescent material, for example, quenching of smartprobes. Any quenching of the fluorescent material may be less than quenching that may occur under continuous illumination. Each fluorescent material may have a chance to recover after illumination under light of a particular colour, before it is illuminated by that light again.

Figure 3:
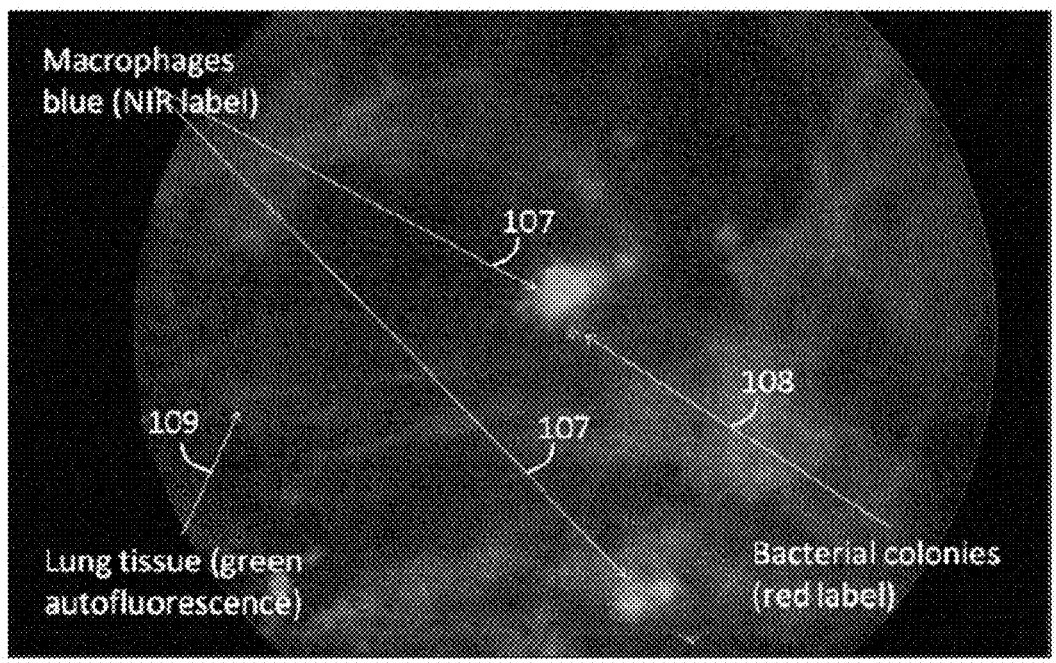
FIG. 3 represents an image demonstrating ex vivo lung tissue imaging in three colours.

FIG. 3 is an image demonstrating imaging of multiple biological targets in ex vivo human tissue at clinically relevant frame rates (in this case, 10 fps). The effect of cores in the image may be observed in FIG. 3 (the image looks like it is made up of dots). In some circumstances, the core-to-core spacing of the fibre bundle 40 may limit the resolution of images obtained using the system of FIG. 1.

The image of FIG. 3 is obtained using the system of FIG. 1 with first and second smartprobes as described above. FIG. 3 is a three-colour image generated from first, second and third sets of image data obtained under illumination by excitation signals from light sources 1, 2 and 3 respectively. FIG. 3 show macrophages imaged using an NIR label (indicated by arrows 107), lung tissue green autofluorescence (indicated by arrow 109), and bacterial colonies imaged using a red label (indicated by arrow 108).

Probes may be introduced into the imaging region by any suitable method. For example, the probes may be introduced into the imaging region by spraying a liquid containing the probes into the imaging region.

In the present embodiment, one of the light sources (blue light source 1) is configured to excite lung autofluorescence, and each of the other light sources is configured to excite molecules of a respective smartprobe. In other embodiments, light sources may be configured to excite different probes. For each probe used, a corresponding colour of light source may be selected.

The system of FIG. 1 may be reconfigurable for use with different probes (for example, with probes having different excitation frequencies from those currently used) by changing the light sources and filters. If a different smartprobe is selected for use, that different smartprobe may have a different excitation frequency from a smartprobe for which the system is initially configured. If so, one or more of the light sources may be changed accordingly to a light source with a different frequency. In the present embodiment, the light sources 1, 2, 3 are LED light sources. It may be simple and/or cheap to replace LED light sources. In some circumstances, the multi-band emission filter may be the only custom component required when reconfiguring the system of FIG. 1 to use a different smartprobe. The ability to reconfigure the system may allow adaptability to different medical issues, for example to urgent medical issues.

In some embodiments, a particular frequency of light may excite more than one substance. For example, one frequency of light may excite both autofluorescence and a smartprobe. In such embodiments, light received in a given time interval may comprise a mixture of light emitted by the different substances. Spectra obtained by the spectrometer 64 may be used to distinguish different materials that are excited by the same frequency of light. In some embodiments, a particular substance (for example, a particular smartprobe) may be excited by the light emitted from more than one of the light sources. In some embodiments, image and/or spectroscopy data from more than one colour of light source may be used to image and/or detect a particular fluorescent material.

In one embodiment, a tissue signal and a signal from a smartprobe are close in frequency, both being blue. Two of the LED sources used may also be close in frequency. Fluorescent light emitted in response to the first of the two LED sources comprises a greater part of the tissue signal and a lesser part of the smartprobe signal. Fluorescent light emitted in response to the second of the two LED sources comprises a lesser part of the tissue signal and a greater part of the smartprobe signal. Results from illumination under each of the two LED sources may be combined to obtain information about both the tissue and a disease target or condition corresponding to the smartprobe.

In some embodiments, there may be some background from the fibre and/or from tissue in the response signal received by the camera 80 and spectrometer 64. In some circumstances, data obtained under illumination by one or more of the light sources may be used to remove or reduce background in data obtained under illumination by a further one of the light sources. In some circumstances, what is background for one measurement may be wanted signal for another.

Figure 5A:
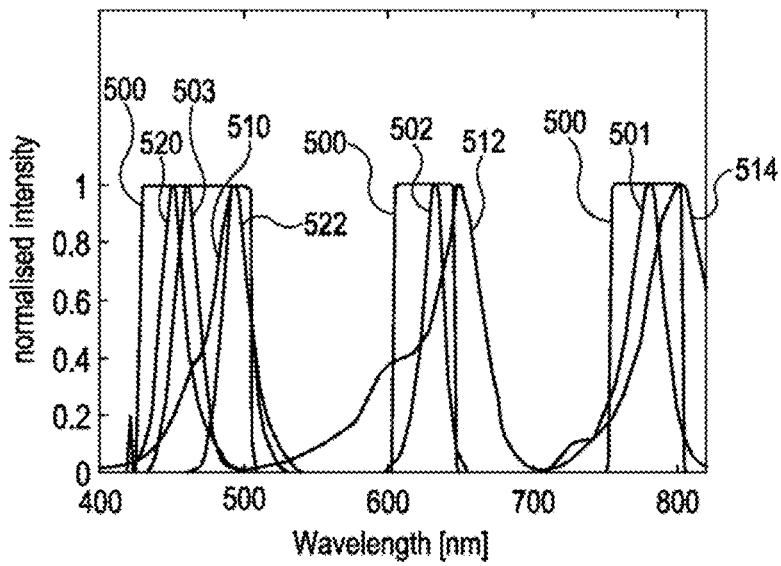
FIG. 5a is a plot of excitation spectra for an embodiment.
Figure 5B:
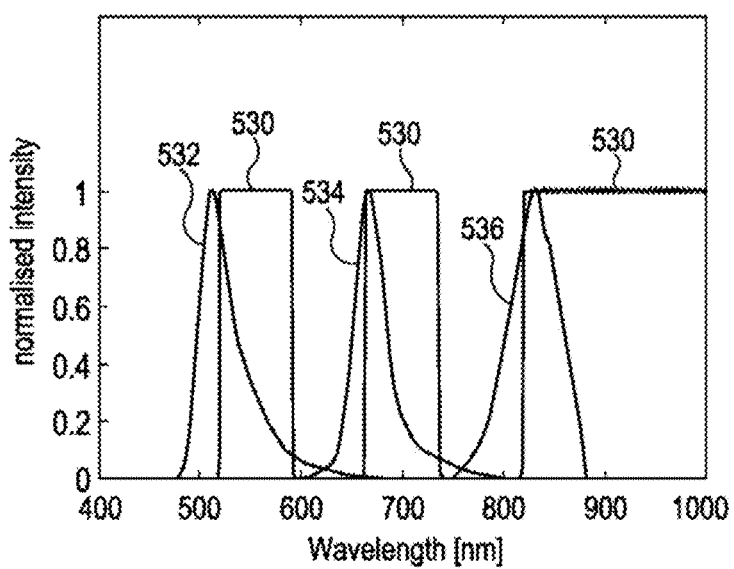
FIG. 5b is a plot of emission spectra for an embodiment.

FIGS. 5a and 5b show plots of spectra obtained using the system of FIG. 1 (although using different fluorophores from those described above).

FIG. 5a is a plot of excitation spectra. Line 500 is an excitation spectrum of the excitation filter 24. Line 501 is a spectrum of blue LED 1 (470 nm). Line 502 is a spectrum of red LED 2 (625 nm). Line 503 is a spectrum of near-IR LED 3 (780 nm).

Line 510 is an absorption spectrum of FITC (fluorescein). Line 512 is an absorption spectrum of Cy5 (cyanine 5). Line 514 is an absorption spectrum of ICG (indocyanine green).

FIG. 5b also shows spectra of a 455 nm LED (line 520) and a 490 nm LED (line 522). FIG. 5b demonstrates the fact that, in some embodiments, multiple LEDs may populate the same excitation filter band. This may allow combinations of LEDs to be used. Autofluorescence emission spectra may not vary as much as fluorophore emission spectra. In some embodiments, both the 455 nm LED and the 490 nm LED may be used to provide autofluorescence. The 490 nm LED may get more FITC signal than the 455 nm. In such embodiments, subtracting the signal from the 490 nm and 455 nm LEDs may allow some of the autofluorescence signal to be removed. A similar approach may be taken in other bands. For example, 617 nm and 660 nm LEDs are widely available.

FIG. 5b is a plot of emission spectra. FIG. 5b shows a spectrum 530 of the emission filter 50. The emission spectrum of FITC (fluorescein) is represented by line 532. The emission spectrum of Cy5 (cyanine 5) is represented by line 534. The emission spectrum of ICG (indocyanine green) is represented by line 536. ICG has been clinically approved but in some circumstance may be a poor label. ICG may be used for blood vessel labelling. The system of FIG. 1 may detect ICG down to 5 nM concentration.

In the present embodiment, the FITC emission peak is missed, but a large fraction of the FITC emission is captured. The Cy5 emission peak is just about captured.

Cy5 and fluorescein derivatives may often be used as fluorophores in smartprobes. When conjugated to a functional part of the smartprobe, the fluorophore may experience a shift in absorption and emission spectra, for example a shift not larger than 5 to 10 nm.

In the present embodiment, three light sources are multiplexed. In other embodiments, four light sources are multiplexed. In further embodiments, five or more light sources are multiplexed. The number of disease targets that can be imaged and/or detected may increase with the number of light sources used.

The combination of three-colour imaging with spectroscopy may allow more than three disease targets to be distinguished using three colours of light, since the spectra obtained by the spectrometer may allow different substances that fluoresce at similar wavelengths to be distinguished.

In some circumstances, shape may be used to distinguish between different disease targets that fluoresce in response to the same frequency of excitation light. For example, in some circumstances shape may be used to distinguish between bacteria and cells. In some embodiments, sets of image data from the camera 80 may be automatically analysed to determine the shape of features within that image data. In some embodiments, an image corresponding to one or more sets of image data may be displayed to a user for the user to identify disease targets by shape. In some circumstances, the use of 4 LEDs may allow up to 8 variables (and therefore for up to 8 disease targets to be distinguished) if shape is also used.

A multi-colour image (for example, the three-colour image of FIG. 3) may allow a user to view a combined image of physiology (tissue structure) and pathology (for example, the presence of bacteria and/or neutrophils) in a single image. The user may have more information about the distal lung environment than may be obtained with, for example, white light endoscopy. Smartprobes may be selected for imaging of any appropriate pathology or features. Any appropriate combination of smartprobes may be used.

It has been shown that smartprobes may be deployed alongside pulmonary microendoscopy in vivo to image disease relevant targets. In the present embodiment, smartprobes are coupled with a miniature fibre-optic imaging bundle to access distal alveolar regions and transmit an image from a distal end of the fibre bundle to the rest of the optics.

Fluorescence endoscopy may be enhanced by integrating smartprobes in multi-colour scenarios. The use of smartprobes may allow information to be obtained about the tissue being imaged that would not be obtainable without the smartprobes. The use of more than one type of smartprobe, for example smartprobes emitting different colours of light, may allow still further information to be obtained. In some circumstances, smartprobes may be used that detect chemical activity.

The system of FIG. 1 may extend the use of molecular imaging to image multiple disease targets concurrently. The system of FIG. 1 may be used to obtain immediate information that may be used to determine the absence or presence of bacteria or markers of inflammation such as infiltrating innate immune cells (for example, monocytes and neutrophils) associated with suspected pneumonia in critically ill patients.

Disruptive optical technologies, for example microendoscopy using smartprobes as described above, may have high impact in clinical practice. For example, such technologies may have high impact in the rapid diagnosis of lung inflammation and infection in critically ill ventilated patients.

The system of FIG. 1 may provide real-time information about the state of the distal lung. By performing real-time imaging and detection, diagnosis may be performed while conducting a microendoscopy procedure rather than waiting for lab results. A speed of diagnosis may be improved, allowing appropriate treatment to be delivered to the patient without delay.

The system of FIG. 1 is configured to provide imaging at video rate. The real-time information obtained from the system of FIG. 1 may also include spectroscopy information. The information may be provided quickly and cheaply.

In some embodiments, camera-based microendoscopy systems such as that of FIG. 1 may provide faster imaging than some confocal-based microendoscopy systems, since no scanning may be required by the camera-based microendoscopy systems. Camera-based systems may provide a robust and economical route to multi-colour fluorescence detection.

A widefield endoscopic imaging system may allow greater depth to be sampled than a confocal system, especially in the near IR. Even though the system of the present embodiment may not be able to image in depth, clinically it may be used to detect the presence of disease targets. The presence of a signal, for example a near IR signal, may be used to inform a measured presence of disease targets at depths of, for example, 0 µm to 200 µm.

The system of FIG. 1 may be scalable. In some circumstances, it may be straightforward to add an additional light source to the system of FIG. 1. An additional light source may allow an additional smartprobe to be used. An additional light source may allow one or more further disease targets to be distinguished.

The system of FIG. 1 may be reconfigurable. In some circumstances, it may be straightforward to replace one of the light sources with a light source of a different frequency. The emission filters may also be changeable. A change in light source may allow one of the smartprobes used to be exchanged with a different smartprobe, for example to image a different disease target. If a new smartprobe is developed, the system of FIG. 1 may be reconfigured to operate with that smartprobe. In some embodiments, the system of FIG. 1 may be used to calibrate new smartprobes. If a new LED source is developed, for example an LED that more closely matches the excitation frequency of a particular smartprobe, the system may be reconfigured to use that LED source.

Using LEDs as light sources may allow triggering for multi-colour capability. Some other light sources, for arc lamps and supercontinuum sources, are broadband but emit all wavelengths at the same time and therefore in some cases may not be individually triggered in the way described above.

The system of FIG. 1 has been used across a 400 nm band between 450 nm and 850 nm. A single detector may be used across a bandwidth of 400 nm or more. In some embodiments, multiple iterations of the system of FIG. 1 may be used, each having a different bandwidth, thereby increasing the bandwidth of a combined system.

The system of FIG. 1 has no moving parts, which may allow the system to be stable, compact and/or cheap.

The triggering of the different light sources in sequence may allow fast multi-colour endoscopy in the detection path. The switching on and off of the light sources 1, 2, 3 may reduce spectral mixing while allowing flexibility to adapt to scenario required. The software, electronic and most of the optics may be kept the same while changing the LEDs and filters to adapt to different fluorophores.

The switching on and off of the light sources may reduce or eliminate quenching of the smartprobes.

In the embodiment of FIG. 1, the same fibre cores are used to collect light for both imaging and spectroscopy. A single fibre bundle 40 is used. The light used for spectroscopy follows the same optical path as the light used for imaging. By using a single fibre bundle 40 for acquiring light for both imaging and spectroscopy, the complexity of the system of FIG. 1 may be reduced.

In the system of FIG. 1, the aperture controls 25, 52 may be used to select a part of the field of view of the fibre bundle 40. In the present embodiment, the diameter of the field of view of the fibre bundle is 600 µm. The aperture controls may be manual or motion controlled. The aperture controls 25, 52 may be used to locate a region within the field of view. The system may then perform imaging and/or spectroscopy on the selected region. In some embodiments, a user may identify a feature of interest within the field of view. The aperture controls may be used to select a part of the field of view comprising the feature of interest.

The system of FIG. 1 may be adaptable to dark field endoscopy and/or to white endoscopy by manipulation of the apertures of FIG. 1. In some embodiments, dark field reflectance microscopy is achieved by providing ring illumination from all light sources, from a subset of the light sources, or from a single light source. Ring illumination may be obtained by masking the centre of the illumination by an aperture (for example, aperture 25 of FIG. 1). The ring illumination may then be masked with aperture 52 of FIG. 1, which may allow only scattered light from the dark region to enter the camera 80.

In some embodiments, aperture element 52 may be replaced with a Fourier domain optical filter. By replacing the aperture element with the Fourier domain optical filter, or by any other appropriate filter, the system may be adapted to optical signal processing. The Fourier domain optical filter may remove smooth transitions of background tissue while retaining high optical spatial features which may be used, for example, to identify bacterial structures.

In some embodiments, a user may control aspects of the operation of the system of FIG. 1 using software. For example, the user may control an exposure time so that a shorter or longer exposure is obtained for each image. The user may control a frame rate. The user may control a pulse rate. The user may control a time interval occupied by each excitation signal. The user may control an illumination level.

In some embodiments, parameters such as LED illumination and detection parameters may be adapted to the tissue being imaged. The triggering may use pulse width modulation (PWM) to illuminate tissue more or less. An exposure time of the camera may be adapted to gather an optimal amount of fluorescence.

The system of FIG. 1 comprises both a monochrome camera 80 and a spectrometer 64. In other embodiments, the spectrometer 64 is omitted from the system.

A system with one camera configured to receive light from the multiple light sources may be referred to as a single-camera system (whether or not that system also comprises a spectrometer). A single-camera multi-colour system may be configured to distinguish different disease targets by colour and/or shape.

In some circumstances, a system having a single steady-state camera may provide time-multiplexed multi-colour imaging while being small and cheap and while working over a wide wavelength range, for example 500 nm to 900 nm. A system using three-colour fluorescence may be able to distinguish at least three targets. In different systems, more than three colours may be used.

The system of FIG. 1 is configured to perform steady-state imaging and spectroscopy. The camera 80 is a steady-state camera. For each excitation signal (for example, a 30 ms excitation signal), the camera 80 receives fluorescent light for a time interval corresponding to the time interval occupied by the excitation signal (for example, 30 ms) and uses fluorescent light received over the whole of that time interval to generate a set of image data. The set of image data is representative of the amount of fluorescent light received by each pixel during the time interval. The light sources 1, 2, 3 are continuous-wave LEDs that emit light continuously during each pulse. For example, a given LED may emit light continuously for each 30 ms time interval in which it is turned on.

A system having a single steady-state camera and steady-state spectroscopy may acquire time-multiplexed spectra in addition to time-multiplexed imaging. Each image may have at least one associated spectrum. In some circumstances, the addition of spectra may help to disentangle target probes and enzyme activity probes. Molecular imaging may become stronger. The system may provide a double view of a specimen, showing how the specimen looks and how at least one spectrum corresponding to the specimen looks. The system may be scaled over many colours.

In other embodiments, the system is configured for time-resolved operation. The system may be configured to perform fluorescence-lifetime imaging microscopy (FLIM). Fluorescence-lifetime imaging microscopy uses a decay time of a fluorescence signal to obtain additional information about the tissue being imaged than may be obtained using steady-state imaging. The system may also be configured to perform time-resolved spectroscopy.

Different molecules may have different fluorescence lifetimes. This may be true even of molecules that emit the same colour of fluorescent light when excited by light of a given frequency. By using FLIM, different targets may be distinguished that in some cases may not be distinguished using steady-state imaging, for example steady-state multi-colour imaging as described above. For example, in some circumstances, green light from smartprobes may be distinguished from green light caused by the autofluorescence of tissue. In some circumstances, FLIM may be used to distinguish between dead tissue and alive tissue. FLIM may be used to measure the lifetime of any suitable probe that may be put into the tissue. The probe may be used to measure a condition of the tissue, for example to measure tissue pH. The probe may change its lifetime under different conditions.

In embodiments of a time-resolved system, each light source is a pulsed or modulated light source. Each excitation signal comprises light that is pulsed or modulated at a much higher rate than the length of the excitation signal. The pulsed or modulated light source may have a nanosecond or picosecond pulse or modulation rate. The pulse or modulation rate may be, for example, between 1 MHz and 100 MHz.

For example, in one embodiment, light sources 1, 2, 3 of FIG. 1 are replaced by pulsed light sources, each having a pulse length of 500 ps. Each light source is turned on for a respective time interval of 30 ms as shown in FIG. 2*b*. In the 30 ms time interval for which the LED is turned on, the LED emits a large number of 500 ps pulses.

Each light source may comprise any suitable pulsed or modulated light source, for example a nanosecond to picosecond pulsed LED, nanosecond to picosecond pulsed laser source, or a modulatable LED.

The camera 80 may be replaced or supplemented by a time-resolved detector. The time-resolved camera may comprise, for example, a time-gated intensified CCD camera, time-gated intensified CMOS camera or CMOS SPAD array. For example, the time-resolved detector may be a 32×32 array, 64×64 array or 128×128 array of CMOS time-resolved SPADs.

The time-resolved detector is configured to record the time of arrival of fluorescent light. For example, the time-resolved detector may be configured to record a time of arrival for each photon it receives using time-correlated single photon counting (TCSPC). The time-resolved detector may be synchronised with the pulsing of the light source.

The determined time of arrival for each photon may be a time relative to a time of a picosecond light pulse that caused the emission of that photon.

In one embodiment, the time-resolved detector is a 32×32 array of SPADs. Each photon received by the array of SPADs is recorded individually. Its time of arrival and an arrival position is recorded (for example, the arrival position may correspond to a position of an array element at which the photon arrived).

For each element of the time-resolved detector, the times of arrival of the photons received by that element may be plotted (for example, as a histogram) to determine a fluorescence lifetime. In other embodiments, any suitable method of determining the fluorescence lifetime from the detection of photons by the time-resolved detector may be used. The time-resolved detector generates a set of image data in which the intensity of each pixel is representative of a determined fluorescence lifetime for a corresponding detector element.

The spectrometer may also determine time-resolved spectra. In some embodiments, a combination of time-resolved imaging and time-resolved spectroscopy may be used to image and/or detect different disease targets.

Figure 6A:
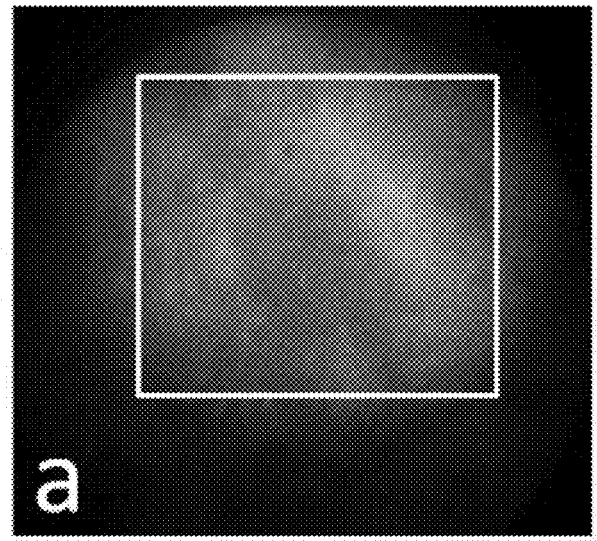
FIG. 6a shows a steady state camera image of ex vivo human lung tissue.
Figure 6B:
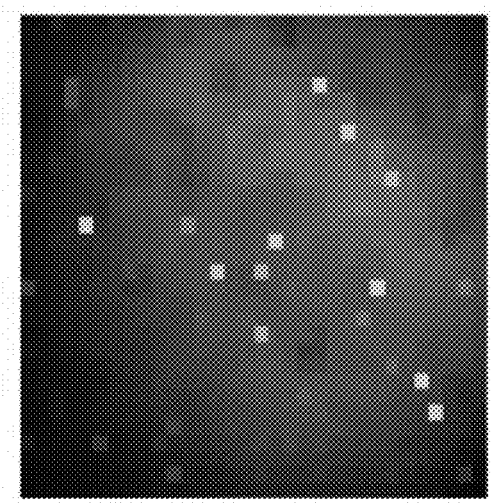
FIG. 6b shows a single photon counting image obtained using a Megaframe camera.
Figure 6C:
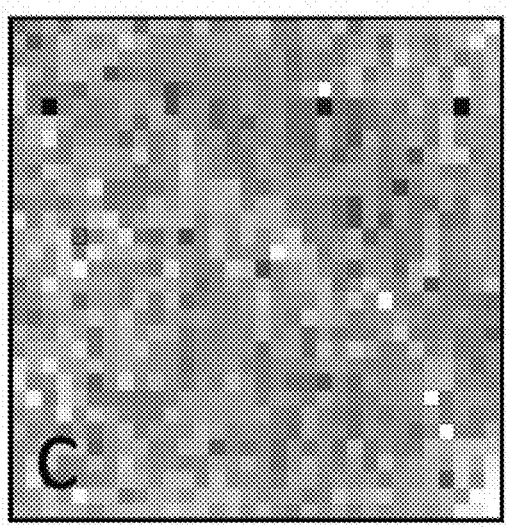
FIG. 6c shows a FLIM image obtained using a Megaframe camera.
Figure 6D:
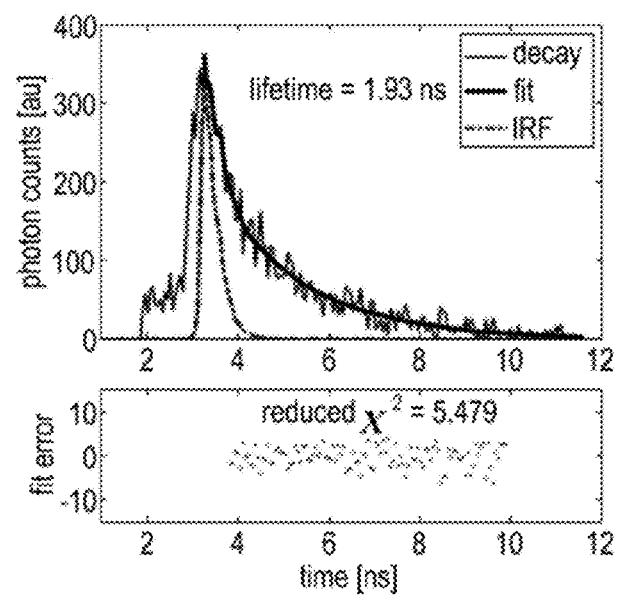
FIG. 6d is a plot of sample decay from lung tissue.

FIG. 6a shows a steady state camera image of ex vivo lung tissue obtained using the system of FIG. 1. FIGS. 6b to 6d demonstrate a capability of a modified version of the system of FIG. 1 to perform FLIM on ex vivo human tissue. In the modified version of FIG. 1, the light sources 1, 2, 3 are replaced with pulsed LEDs having a pulse length of 500 ps. The camera 80 is replaced by a Megaframe camera. The Megaframe camera comprises a 32×32 SPAD array. The Megaframe camera is configured to image at a frame rate of 1000 or more fps. The Megaframe camera operated by using time-correlated single photon counting (TCSPC).

FIGS. 6b to 6d show results obtained using the Megaframe camera instead of the steady-state camera 80. The results of FIGS. 6b to 6d were obtained from a FLIM acquisition taking 5 seconds. In further embodiments, the FLIM acquisition may be shorter, for example 2 seconds.

In some embodiments, FLIM acquisition is performed using a 250 ms trigger for each FLIM image per colour band. Depending on the fluorophore, the trigger time may be shorter or longer. FLIM acquisition may be accelerated by use of better detectors and sources. Triggering and sequencing may be used for FLIM and/or for time-resolved spectroscopy, using any suitable trigger times.

FIG. 6b shows a single photon counting image obtained using the Megaframe camera. A single photon counting image may be an image in which each pixel intensity value is representative of the number of photons received by a detector array element corresponding to that pixel.

FIG. 6c shows a FLIM image obtained using the Megaframe camera. A FLIM image may be an image in which each pixel intensity is representative of a determined fluorescence lifetime for photons received by a detector array element corresponding to that pixel.

FIG. 6d is representative of a sample decay from lung tissue. The dark solid line in FIG. 6d is representative of the measured decay. The light solid line in FIG. 6d is representative of a fit to the measured decay. The dash-dotted line is representative of the instrument response function (IRF). In the plot of FIG. 6d, the fluorescence lifetime is determined to be 1.93 ns.

The results of FIGS. 6c and 6d were obtained using time-domain FLIM. In other embodiments, the system is configured to perform frequency-domain FLIM. The time-resolved detector may be any camera modulatable for frequency domain FLIM. The light sources are configured to produce modulated light. For example, the light sources may be modulatable LEDs.

The light produced by each of the light sources varies in frequency over a nanosecond to picosecond time scale. The fluorescent light emitted by the imaging region has a corresponding frequency variation. The variation in frequency of the fluorescent light may be used to determine a fluorescence lifetime. The fluorescence lifetime may be determined using a lock-in method.

By obtaining fluorescence lifetimes, different materials may be distinguished, even if those materials emit the same colour of light. A combination of FLIM with steady-state imaging and/or with spectroscopy may allow additional disease targets to be imaged and/or detected. A combination of FLIM with steady-state imaging and/or with spectroscopy may allow further conditions of tissue in the imaging region to be determined in addition to imaging/detection of disease targets. For example, pH of the imaging region may be determined.

Systems using FLIM may be more expensive than steady-state systems since pulsed light sources (for example, pulsed lasers) are needed. However, in some circumstances the increased cost may be justified by a gain in improved multiplexing of probes. Modulated or pulsed LEDs may be less expensive than pulsed lasers. Modulated or pulsed light sources (for example, modulated or pulsed LEDs) may be combined with either a modulated camera or a synchronised time-resolved camera (for example, CMOS SPAD array or time gated camera).

In some embodiments of a time-resolved system, the steady-state camera 80 is replaced by a time-resolved detector and the spectrometer 64 is replaced by a time-resolved spectrometer. For each target, the system may provide time-resolved spectra and imaging. Spectra and imaging may be combined in many different ways to distinguish many probes, for example more than 12 probes for a 3- or 4-colour system.

In other embodiments, the steady-state camera 80 may be replaced by a single detector configured to perform both steady-state imaging and FLIM. For example, a time gated intensifier coupled to a sCMOS or EMCCD camera may be used to provide both steady-state imaging and FLIM.

In other embodiments, the system comprises both a steady-state camera 80 and a time-resolved detector. For example, in some embodiments, the time-resolved camera replaces the spectrometer 64 in the system of FIG. 1.

In some circumstances, providing a time-resolved detector that is separate from the steady-state camera 80 may allow each detector to be chosen for its level of performance in one dedicated function, rather than making compromises between steady-state and time-resolved performance. For example, in some circumstances, the time-resolved detector may have poorer performance in steady-state imaging than a dedicated steady-state camera would have. In some circumstances, the steady-state camera used may be an off-the-shelf camera, which may be cheap. The provision of a time-resolved detector and a separate steady-state camera may allow both good time-resolved imaging and good steady-state imaging to be performed by the system at reasonable cost.

A combination of steady-state imaging and FLIM may be used to provide multi-colour FLIM. Several targets may be time-multiplexed. With the use of FLIM, 2 or more targets per colour may be multiplexed. For example, if FLIM allows 3 targets per colour to be multiplexed, 9 targets may be multiplexed using 3 colours. In some circumstances, different targets may be distinguished more effectively with FLIM than by using spectroscopy.

A steady-state camera and a FLIM camera may be used in a time-multiplexed multi-colour scenario to enable colocalized multicolour images, allowing many probes to be distinguished.

In other embodiments, the system comprises a steady-state camera 80, a time-resolved detector, and a spectrometer 64. Fluorescent light may be split between the steady-state camera 80, time-resolved camera, and spectrometer 64, for example by adding an extra beam splitter.

In some embodiments, the system does not comprise a spectrometer. The system may be a single camera solution including imaging only (which may be steady-state, time-resolved, or both).

In some embodiments, the system comprises a steady-state camera and a time-resolved spectrometer. For example, the spectrometer 64 of FIG. 1 may be replaced by a time-resolved spectrometer without replacing the steady-state camera 80 of FIG. 1. The use of the time-resolved spectrometer may allow a better spectral view. Each image will have associated time-resolved spectra, which may allow multiple probes per colour channel to be disentangled.

In the embodiments described above, a single fibre bundle 40 is used. However, in other embodiments, a plurality of fibre bundles 40 may be used. For example, different fibre bundles 40 may be inserted into different working channels of an endoscope. In some embodiments, different fibre bundles 40 may image in different frequency ranges, thus increasing the overall frequency range imaged by the system.

Figure 7A:
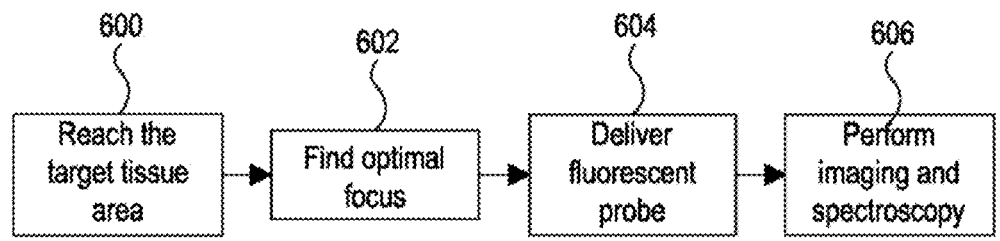
FIG. 7a is a flow chart representing in overview a method of an embodiment.

FIG. 7a is a flow chart representing an embodiment of a method of use of the system of FIG. 1. At stage 600, the fibre bundle 40 is delivered to a target tissue area. At stage 602, optimal focus is found, for example by obtaining repeated images and assessing the images (either automatically or by a user). At stage 604, fluorescent molecular imaging probes are delivered to the target area. At stage 606, imaging and spectroscopy are performed.

Figure 7B:
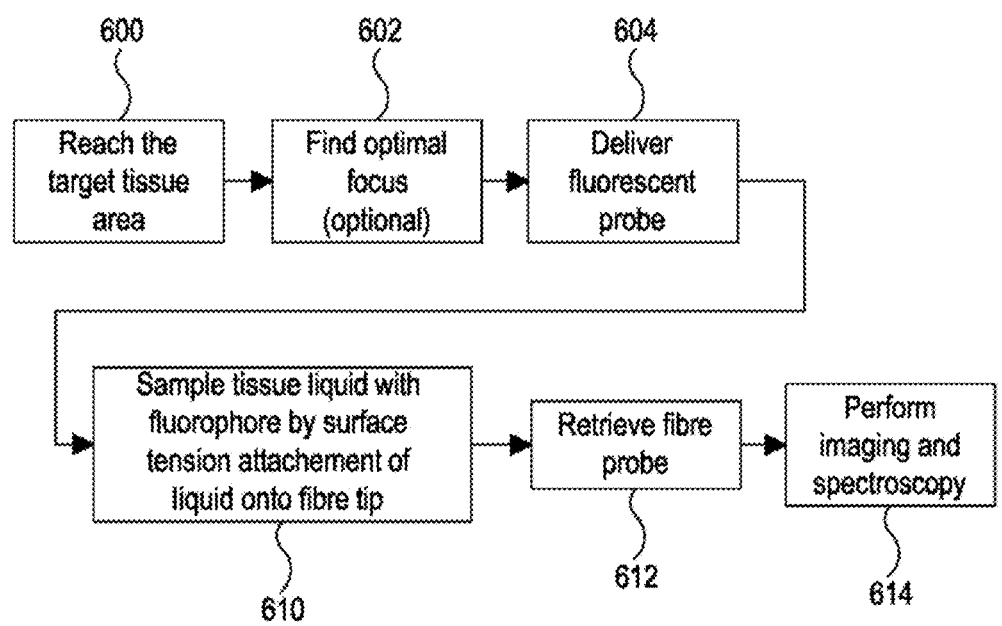
FIG. 7b is a flow chart representing in overview a method of a further embodiment.

FIG. 7b is a flow chart representing an embodiment of a further method of use of the system of FIG. 1. Stages 600 to 604 are the same as for the method of FIG. 7a. At stage 610, tissue liquid is sampled by surface tension attachment of liquid onto the fibre bundle tip (droplet attachment). At stage 612, the fibre bundle 40 is retrieved (i.e. removed from the bulk of the tissue liquid), with a drop of tissue liquid being attached to the fibre bundle tip. At stage 614, imaging and spectroscopy are performed on the drop of tissue liquid. The drop is then removed from the fibre bundle tip by smearing the tip on the surface area of some neighbouring tissue. In other embodiments, stage 602 may be omitted.

In some circumstances, droplets readily attach to the fibre bundle tip. In some circumstances, the use of droplets may provide a substantially background-free view of enzyme activity and/or of the presence of bacteria or of another target.

In some circumstances, tissue background may be wanted. For example, tissue background may be used for navigation to a desired segment and structure. However, once the fibre bundle tip is positioned in the desired segment and structure, it may be useful to remove the background. Functional imaging rather than structural imaging may be performed.

Using the system of FIG. 1, tissue background (autofluorescence) may be reduced or removed in several different ways. The background may be reduced or removed by using droplet attachment. The background may be reduced or removed by deploying several LEDs of similar colour, for example by deploying several blue LEDs. The background may be reduced or removed by using a Fourier domain optical filter which in some circumstances may act as a high pass spatial filter for background reduction or removal. In some instances, the background may be reduced or removed by using FLIM imaging.

Figure 8:
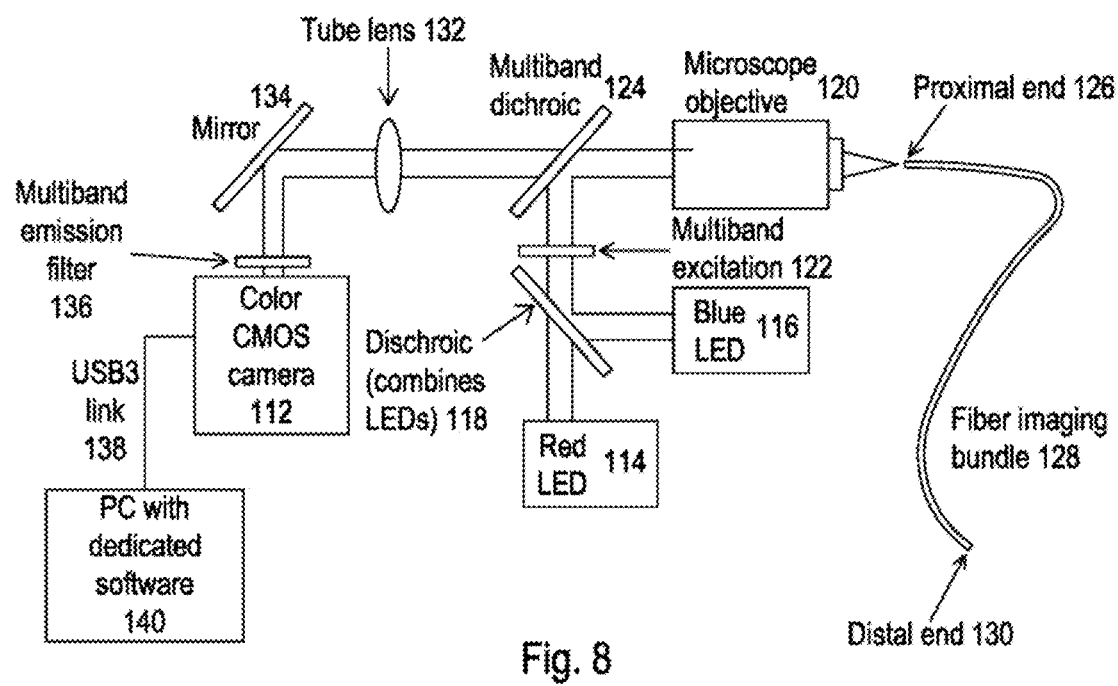
FIG. 8 is a schematic illustration of a two-colour fluorescence system.

FIG. 8 relates to a further system for fluorescence microendoscopy. The system of FIG. 8 comprises a colour CMOS camera 112, red LED 114, blue LED 116, microscope objective 120, multi-band emission filter 122 and multi-band dichroic mirror 124. The system of FIG. 8 further comprises a fibre imaging bundle 128 having a proximal end 126 coupled to the microscope objective 120, and a distal end 130 used for imaging the distal lung. The system of FIG. 8 further comprises a tube lens 132, mirror 134, and multi-band emission filter 136. The colour CMOS camera 112 is coupled by a USB3 link 138 to a PC 140 with dedicated software.

The system of FIG. 8 is a two-colour fluorescence system. The system may be considered to be based on a single-color fluorescence endoscopy platform with the fluorescence filter-set exchanged for that of an integrated two colour, green and red fluorescence spectral range.

In brief, two LEDs 114, 116 are combined with dichroic mirror 118 and illumination is sent to the microscope objective 120 via the excitation filter 122 and another two-band dichroic mirror 124. Fluorescence from the imaging bundle 128 is focused on the colour CMOS camera 112 via a tube lens 132 of 200 mm focal length. An image is collected on the colour CMOS camera 112.

We turn to further details of the components of the system of FIG. 8 and their operation. In the system of FIG. 8, all components are off-the-shelf commercial items. In other systems, any suitable components may be used.

Two LEDs are used to provide illumination: red LED 114 and blue LED 116. Blue LED 116 provides illumination at 470 nm and red LED 114 provides illumination at 625 nm. In the system of FIG. 8, the LEDs used are M470L3 and M625L3, Thorlabs, USA. In other systems, different LEDs may be used. In some systems, more than two LEDs may be used.

Light from the LEDs 114, 116 is collimated using achromatic condenser lenses (not shown). In the present embodiment, the condenser lenses are ACL2520-A, Thorlabs for 470 nm LED 116 and ACL2520-B, Thorlabs for 625 nm LED 114. FIG. 7 is a plot including LED spectra for red LED 114 and blue LED 116. The spectrum for blue LED 116 is dashed line 140 of FIG. 9. The spectrum for red LED 114 is dashed line 142 of FIG. 9.

The collimated beams from the two LEDs 114, 116 are combined using a dichroic beamsplitter 118 (which in the present embodiment is a FF506-D103-25X36, Semrock, USA).

Two-colour epi-fluorescence is achieved using a two-colour filter-set, which in the present embodiment comprises an emission filter 136, dichroic mirror 124 and excitation filter 122 in XF454, Horiba, UK. Two-colour light from the dichroic beamsplitter 118 is passed through the excitation filter 122 and directed by dichroic mirror 124 to a microscope objective 120.

In the present embodiment, the microscope objective 120 is an infinity corrected microscope objective with numerical aperture (NA) 0.3 and working distance 10 mm (RMS10x-PF, Thorlabs, USA).

Figure 9:
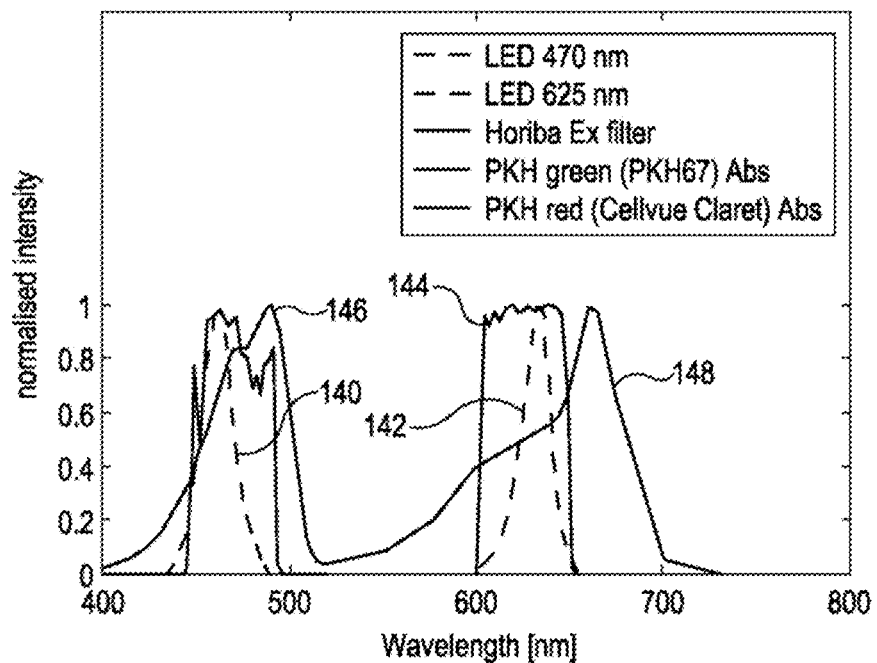
FIG. 9 is a plot of LED source spectra and emission filter absorption curves for the system of FIG. 8.

A spectrum of the excitation filter 122 is shown as line 144 in FIG. 9. In the present embodiment, the fluorophores used are PKH67 and Cellvue® Claret. FIG. 9 also shows normalized absorption spectra for PKH67 (line 146 of FIG. 9) and Cellvue® Claret (line 148 of FIG. 9).

Figure 10:
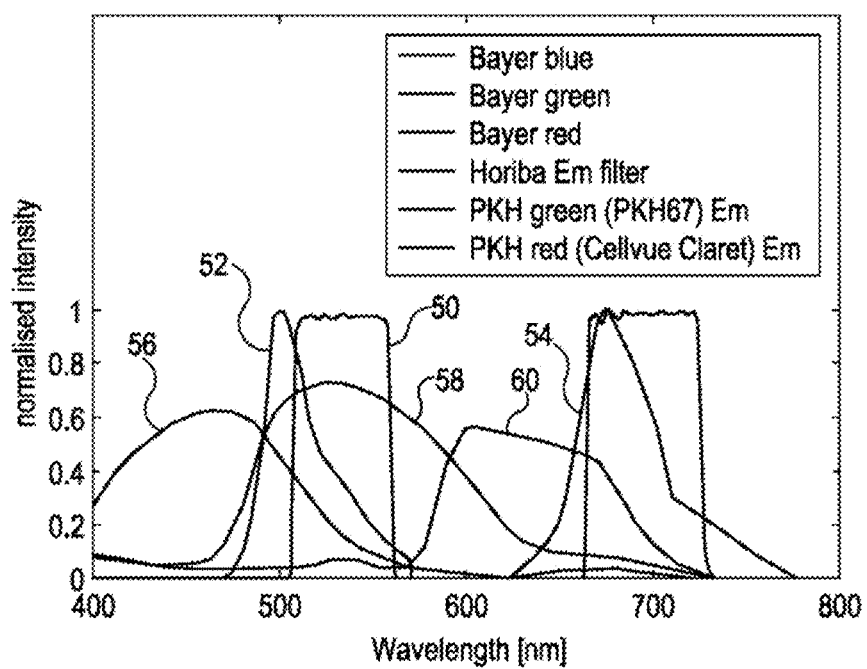
FIG. 10 is a plot of fluorescence emission curves overlaid with emission filter and Bayer filter curves for the system of FIG. 6.

FIG. 10 shows a spectrum of the emission filter 136 as line 150. FIG. 10 also shows normalized emission spectra of PKH67 (line 152 of FIG. 10) and Cellvue® Claret (line 154 of FIG. 10). The fluorescence emission curves 152, 154 are overlaid with the emission filter spectrum 150 and Bayer filter spectra. Bayer blue, green and red are shown by lines 156, 158 and 160 respectively.

From the microscope objective 120, light from the LEDs is passed into the proximal end 126 of a fibre imaging bundle 128. In the present embodiment, the fibre imaging bundle 128 is Alveoflex™, Mauna Kea Technologies, Paris, France. FIG. 11a is an image of the Alveoflex™ fibre imaging bundle 28 as acquired by the camera. FIG. 11b is a zoomed inset of the image of FIG. 11a, showing fibre cores (bright) and cladding (dark regions between the cores). The image of FIG. 11a was acquired at full resolution (1920×1200) in monochromatic mode to improve sampling of the cores.

The proximal end 126 of the fibre imaging bundle 128 (Alveoflex™, Mauna Kea Technologies, Paris, France) is brought to the focus of the objective 120 by mounting it onto a 30 mm caged Z axis translation mount (not shown: SM1Z, Thorlabs USA) enabling fine focusing and optimized coupling of the image from the distal end 130 of the fibre to the rest of the optics. Alveoflex™ imaging fibre 128 has approximately 30,000 cores and 0 mm working distance (i.e. contact imaging), so only fluorescence from the tip 130 of the fibre is well imaged.

In use, filtered light from the LEDs is passed down the fibre imaging bundle 128 into a sample (not shown). In the system of FIG. 8, light from the two LEDs is provided simultaneously. The sample fluoresces. Emitted light from the sample passes up fibre imaging bundle 128 to the microscope objective 120.

Fluorescence exiting the microscope objective 120 is imaged onto the colour CMOS camera 112 (in the present embodiment, GS3-U3-23S6C-C, Grasshopper3, Point Grey Research, Canada). The camera 112 has a universal serial bus 3 (USB3) connection to the computer allowing up to 162 frames per second (fps) at full resolution 1900×1200.

The colour CMOS camera 112 comprises a colour filter (not shown). In the present embodiment, the colour filter is the standard Bayer pattern filter (for which curves 156, 158 and 160 are shown in FIG. 10) that may be deployed in many consumer, machine vision and microscopy cameras. The CMOS camera sensor is a Sony IMX174 which has 7 photoelectrons (e−) read noise.

We refer to the green and red channel as the green (510 nm to 560 nm) and red fluorescence (660 nm to 700 nm) as captured from the setup onto the camera and filtered by the Bayer filter on the CMOS chip. As shown on FIG. 10, the Bayer colour filter (Bayer green, 58) overlaps with the green channel of the two colour filter-set used (XF454, Horiba, UK; line 50), while the overlap in the red channel is smaller (Bayer red, 60; emission filter, 50). Smaller overlap in the red channel is offset by greater separation of the two channels (the green channel and red channel are separated by around 100 nm) which may reduce spectral mixing.

The architecture of FIG. 8 may extend standard widefield endoscopy to dual-colour whilst taking advantages of improved imaging and illumination technologies.

The system performance of the system of FIG. 8 has been characterized by measuring the spatial resolution, the spectral throughput of illumination and fluorescence collection, chromatic focus shift, verification of the camera read noise and performance at high frame rate acquisition (e.g. >30 fps). The aim is to achieve an optimal contrast on targets ranging in size from bacteria (0.5 μm to 2 μm) to cells, such as monocytes and neutrophils (10 μm to 15 μm), and to fungi (100 μm or more).

The lowest detectable light intensity defines the visibility of the object against the noise floor, while chromatic aberrations may potentially affect contrast levels for each spectral range detected.

A frame rate for assessment in fluorescence microendoscopy may be 10 to 15 frames per second (fps). While 10 to 15 fps may be easily achievable with CMOS camera technologies in terms of speed and noise, one may assess how such frame rates compromise the limit of detection. High frame rates could point to applications of this modality such as tissue elastography and lung compliance on alveolar level.

Spatial resolution was measured by contacting the distal end of the Alveoflex™ fibre 128 to a standard chrome on glass USAF 1951 target (Thorlabs, USA, part number R1DS1N). This measurement was done in transmission (through the USAF target) by allowing the fluorescence from a target (fluorescent block, Chroma, USA) in the spectral range 510 nm to 560 nm to pass through the test target (the USAF target) having been illuminated via the excitation delivered through the Alveoflex™ fibre 28 and the target imaged back through the optical system in the conventional manner. An intensity line profile was taken over the image obtained from the test target (the USAF target) to estimate contrast reduction with increasing resolution.

Spectral throughput measurements were undertaken by inserting a fibre probe connected to the spectrometer (200 μm fibre connected to a USB2000 spectrometer, Ocean Optics, USA) on the following locations: 1) distal side 130 of Alveoflex™ 128 (in front of a light source), 2) proximal side 126 of Alveoflex™ 128 and 3) the camera imaging plane. The distal end 130 of Alveoflex™ 128 was illuminated by a white LED lamp (not shown). Fluorescence collection efficiency was measured by illuminating the distal end of the fibre 128 by a white LED and measuring the optical power at 1) proximal side 126 of Alveoflex™ 128 and 2) the camera imaging plane.

The limit of detection (LOD) for fluorescein (Sigma Aldrich, USA) and Cy5 (Sigma Aldrich, USA) solutions was determined. 1 nM, 10 nM, 50 nM and 100 nM water solutions were prepared. The Alveoflex™ 128 was inserted into the solution and 10 images were taken for each concentration with the exposure time set to 80 ms. A background image was obtained by illuminating the Alveoflex™ 128 by both LEDs 114, 116 as in normal operation, but without any fluorescence or stray light entering the tip. Fifty background images were saved and their mean subtracted from images acquired from solutions. A 40×40 pixel area was selected from the central area of the Alveoflex™ imaging fibre bundle. Mean and standard deviation were calculated for the 40×40 pixel area, for a single 80 ms exposure time image indicating signal-to-noise (SNR).

Chromatic effects may be particularly relevant for multi-colour fluorescence microendoscopy. Chromatic effects were assessed by loading the distal end 130 of the Alveoflex™ 128 with 0.3% relative intensity standard fluorescence microspheres (green Inspeck™ I-7219 and red Inspeck™ I-7224, Life Technologies, USA).

Fluorescence microspheres in solution may readily attach to the distal tip 130 and this may provide a good target for evaluation of contrast and contrast degradation. To optimize the focus of fluorescence onto the camera, the position of the tube lens 132 was adjusted with respect to the CMOS sensor camera and the position of the proximal fibre end 126 was adjusted with respect to the microscope objective 120. The tube lens 132 was pre-aligned as described in M. Pierce, D. Yu, and R. Richards-Kortum, "High-resolution Fiber-optic Microendoscopy for in situ Cellular Imaging," Journal of Visualized Experiments (2011) and was kept fixed. The proximal end 126 of the Alveoflex™ 128 was moved to 3 locations. Optimal focus for green fluorescence was found and moved +/−5 µm around this location.

Camera read noise was measured by taking 100 bias frames (0 ms exposure time) in dark room conditions with a metal C-mount cap on the sensor. Camera gain was set to 0 dB and the camera video mode to 7 (lowest noise mode for this particular camera). The mean of all bias frames was subtracted from a sample bias frame and the standard deviation provides the read noise in analog-to-digital units (ADU). We used 0.51 e⁻/ADU as the system gain to derive the read noise in e⁻. We also used the monochrome version of the camera sensor for read noise measurements (part number GS3-U3-23S6M-C, Point Grey Research, Canada). Dark noise was measured by taking a 3 second exposure time image in dark room conditions as above. The average bias frame was subtracted from the 3 second exposure frame and the standard deviation of the resulting image was divided by 3 to obtain the dark noise for a 1 second exposure.

For all experiments a background image was acquired prior to imaging sessions and subtracted from the acquired images. No frame averaging or image processing was performed, although the potential improvement of image processing is discussed further below.

An experiment for which results are shown in FIG. 12a and FIG. 12b was performed at 510 nm to 560 nm spectral range, with an 8 bit image, 80 ms exposure time (12 fps), gain 15 dB. FIG. 10a shows the USAF test target with an even fluorescent illumination. FIG. 10b shows a line profile across group 6 elements of the USAF test target where the line thickness of smallest resolvable line (group 6, element 6) is 4.38 µm. Individual test chart lines may be clearly distinguished at this resolution. Fibre core size and spacing may limit the system's spatial resolution and hence image quality (see FIG. 9b for a demonstration of fibre core packing density).

Read noise was measured to be 8 e⁻ and dark noise 1 e⁻/s. As the frame rates used are at least 12 fps, the influence of dark noise may be minimal. The signal may be read noise dominated for the detection of up to about 400 e⁻ where read noise is 35% of the Poisson noise.

The uniformity of the field of view is found to be as follows: for the green channel edge intensity is 54% of the central intensity, for the red channel edge intensity is 76% of central intensity. While future work will need to address the uniformity of the green channel in the current systems this was found not to seriously affect the imaging quality.

The optical power exiting the distal fibre 130 and fluorescence collection efficiency are summarized in Table 1 below.

TABLE 1

Illumination and fluorescence collection efficiency

| Measurement | Result |
|---|---|
| 470 nm LED optical power exiting the distal end of Alveoflex ™ | 1.8 mW |
| 625 nm LED optical power exiting the distal end of Alveoflex ™ | 3.4 mW |
| Fluorescence collection efficiency on green channel | 53.1% |
| Fluorescence collection efficiency on red channel | 52.8% |

The maximum optical power coupling to Alveoflex™ 128 for 470 nm LED is 2.4 mW, but we limit this to 1.8 mW due to the intrinsic red autofluorescence of the Alveoflex™, see fibre background discussion below. For 625 nm LED, the optical power measured at the distal end 130 of the fibre 128 is 3.4 mW. Total optical power is within acceptable limits of maximum exposure as defined in BS EN 60825-1:2007— Safety of laser products. Equipment classification and requirements—BSI British Standards. For fluorescence collection, we measured 53% efficiency for both channels.

Spectral throughput is analysed in FIG. 11. Although spectral attenuation was found not to be significant to the camera plane, the Bayer filter was found to attenuate the red channel.

Figure 13:
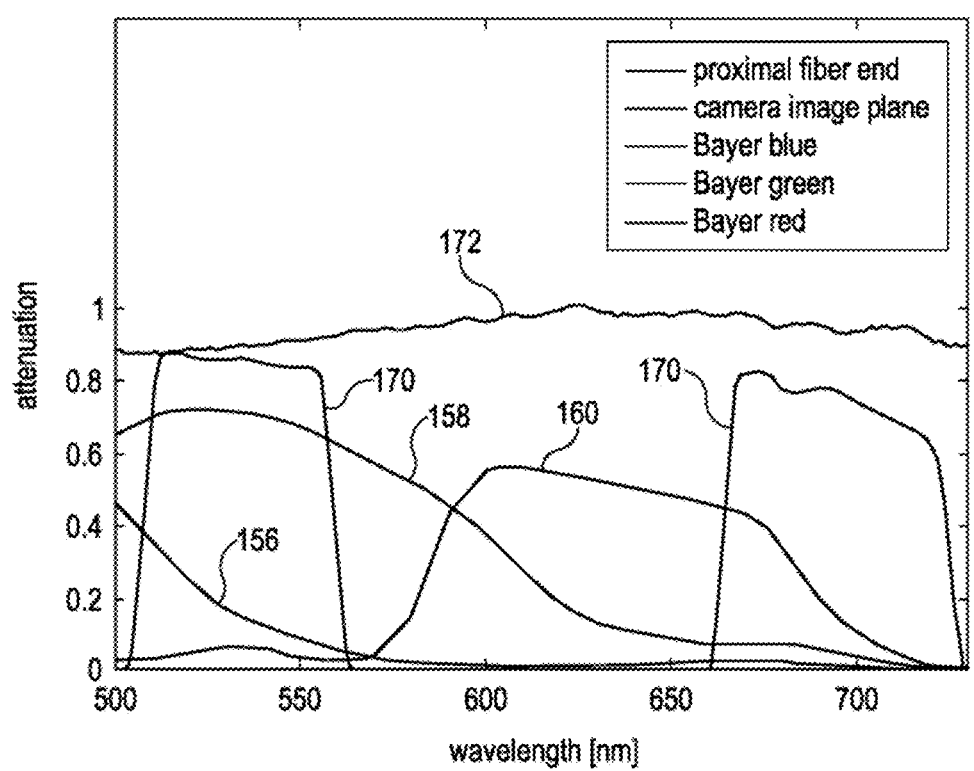
FIG. 13 is a plot of spectral throughput.

Fibre fluorescence throughput is above 85% across the spectral range studied, which is 500 to 750 nm. System fluorescence throughput was measured at the camera image plane (line 70 of FIG. 13) and includes attenuation by the fibre bundle 128, objective 120, dichroic 124, emission filter 136 and the mirror 134. It may reflect what would be expected from the dichroic 124 and emission filters 136 used. Increased attenuation in red may be due to tube lens 132 and microscope objective 120. FIG. 11 shows Bayer filter spectra (lines 156, 158 and 160) superimposed to illustrate an expected reduction of the signal onto the camera. Line 172 represents spectral throughput at the proximal fibre end 126.

SNR analysis of the uniform solutions of fluorescein and Cy5 are given in Table 2.

TABLE 2

SNR for FITC and Cy5 solutions

| Experiment | SNR |
|---|---|
| 1 nM fluorescein | 1.5:1 |
| 10 nM fluorescein | 2.3:1 |
| 50 nM fluorescein | 2.9:1 |
| 100 nM fluorescein | 3.4:1 |
| 1 nM Cy5 | 1.4:1 |
| 10 nM Cy5 | 1.3:1 |
| 50 nM Cy5 | 1.6:1 |
| 100 nM Cy5 | 2.5:1 |

Fluorescein have found to have a LOD concentration of 10 nM and Cy5 was found to have LOD concentration of 50 nM. Some known systems may obtain lower detection limits, for example due to deploying several EMCCD cameras with optimal spectral ranges on each camera. The system of FIG. 8 uses a single colour camera 112 which may have a higher inherent read noise than using individual cameras for each colour. The difference in LOD between cameras was verified by using a scientific CMOS camera (PCO.edge mono 4.2LT, PCO AG, Germany) instead of the GS3-U3-23S6C-C, Grasshopper3 of the system of FIG. 8. Using the scientific CMOS camera, LOD improved to 1 nM for fluorescein and 10 nM for Cy5.

Figures 14A, 14B, 14C:
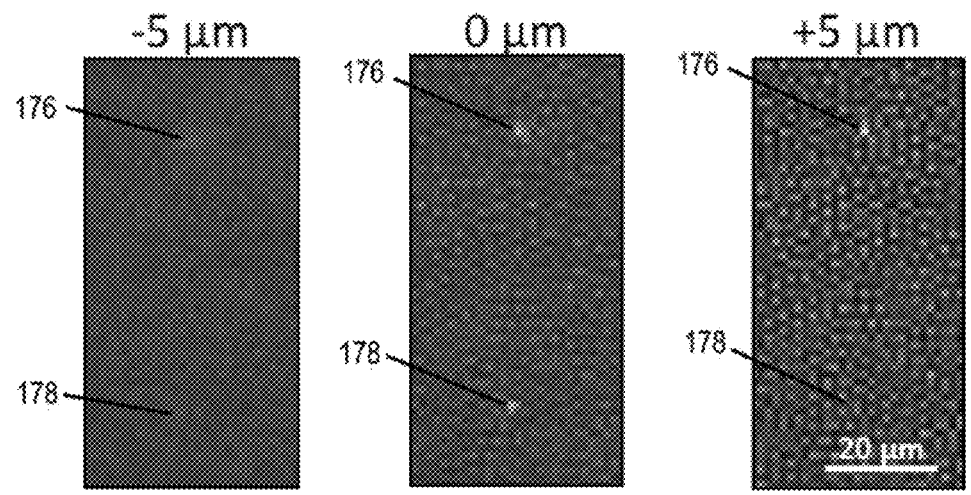
FIGS. 14a, 14b and 14c are images of dots at focal shifts of −5 µm, 0 µm and +5 µm respectively.

FIGS. 14a to 14c show contrast degradation with defocus for green and red fluorescence. A reduction in contrast for individual red and green microspheres is shown. FIGS. 14a to 14c demonstrate the visual appearance of dots at different focus shifts (−5 µm in FIG. 14a, 0 µm in FIG. 14b, +5 µm in FIG. 14c). In each figure, a red microsphere 176 is present at the top of the image and a green microsphere 178 is present at the top of the image. The focus of each of the microspheres 176, 178 changes with the focus shift.

Figure 15A:
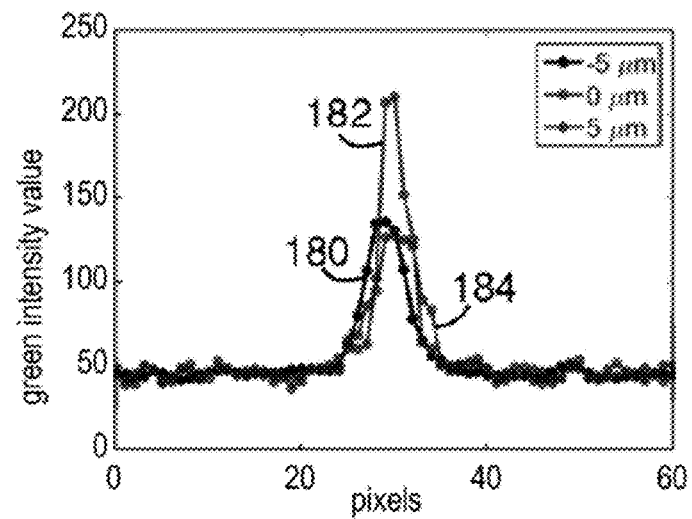
FIG. 15a shows a line profile of a green channel across a green microsphere.

FIG. 13a shows the line profile across the green microspheres on the green channel. Line 180 is the line profile at −5 µm focus shift. Line 182 is the line profile at 0 µm focus shift. Line 184 is the line profile at +5 µm focus shift. FIG. 15a indicates that the 0 µm position may be the optimal focus for green microspheres, judging by contrast.

Figure 15B:
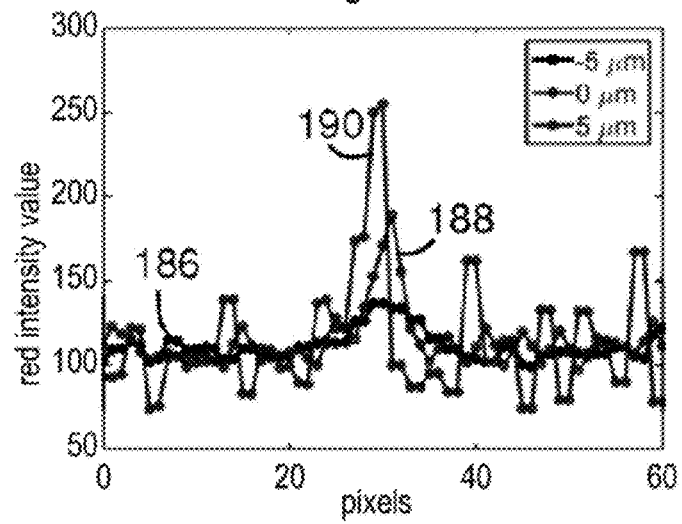
FIG. 15b shows a line profile of a red channel across a red microsphere.

FIG. 13b shows the line profile across the red microspheres on the red channel. Line 186 is the line profile at −5 µm focus shift. Line 188 is the line profile at 0 µm focus shift. Line 190 is the line profile at +5 µm focus shift. FIG. 15b demonstrates that 5 µm may be the optimal focus for the red microspheres. This axial displacement for the red channel over the green channel is likely due to chromatic aberration.

Some imaging fibre bundles have detectable fibre background autofluorescence. The modulation on FIG. 13b for the 5 µm position may be due to red fluorescence from the fibre cores and may provide further evidence that this the 5 µm position is the optimal focus for the red channel.

A compromise may be to place the distal tip of the Alveoflex™ 128 between the two focal locations that were determined to be optimal (0 mm for green and 5 mm for red), which may minimize the chromatic effect with the 0.3 NA microscope objective 120.

Some current methods to determine the bacterial burden in suspected ventilator-associated pneumonia (VAP) rely on the culture of BALF. The growth of colony forming units above $10^4$ per ml (CFU/ml) or $10^5$ CFU/ml may be considered diagnostic of VAP. As bronchoalveolar lavage involves the instillation and retrieval of fluid, a dilution effect may be seen. The true bacterial burden in the infected distal lung may be likely to be $10^5$ to $10^6$ CFU/ml.

To establish the suitability of the system of FIG. 8 for the lower limit of bacterial detection in the distal lung, initial experiments were performed in two scenarios in which microspheres were used as surrogates for bacteria. A first experiment comprised imaging of microspheres alone in black Eppendorf tubes, to avoid tube fluorescence. A second experiment comprised imaging of microspheres in ex vivo lung tissue placed in a well plate.

0.3% Inspeck™ 2.5 µm microspheres (green Inspeck™ 1-7219 and red Inspeck™ I-7224) were used as a fluorescence emission standard indicative of labelled bacteria. Green 0.3% Inspeck™ microspheres may be considered to have the same emission to green OMI smartprobe labelled bacteria (*Pseudomonas aeruginosa*) and red 0.3% Inspeck™ microspheres are 1.5 times weaker than PKH red (Cellvue® Claret, Sigma Aldrich, USA) labelled bacteria (*Pseudomonas aeruginosa*).

Blackened micro-tubes were filled with microsphere concentrations of $10^3$ per ml, $10^4$ per ml, $10^5$ per ml and $10^6$ per ml to derive the detection limit of the system without the lung tissue present. Tubes were centrifuged for 10 seconds before each experiment.

Excised lung tissue was placed in well plates with 0.3% Inspeck™ 2.5 µm microspheres deposited at the following concentrations $10^3$ per ml, $10^4$ per ml, $10^5$ per ml and $10^7$ per ml. Controls included excised lung tissue alone, $10^6$ empty microspheres per ml in lung tissue and distilled water. Each sample was imaged for 30 seconds and the camera settings were set as follows: 8 bit image acquisition, gain 24 dB, exposure time 80 ms (12 fps). Detection of weakly fluorescent microspheres was assessed visually on the acquired image during the 30 s experiment. A successful detection was defined as seeing at least a single target.

FIGS. 16a to 16d demonstrate fast image acquisition of ex vivo lung autofluorescence. FIG. 16a is an image taken at 20 fps using weakly fluorescing microspheres, 0.3% Inspeck. FIG. 16b is an image taken at 20 fps using more fluorescing microspheres, 3% Inspeck. FIG. 16c is an image taken at 200 fps using weakly fluorescing microspheres, 0.3% Inspeck. FIG. 16d is an image taken at 200 fps using more fluorescing microspheres, 3% Inspeck.

While 3% Inspeck™ microspheres are visible at both 20 fps and 200 fps (arrows 200 in FIGS. 16b and 16d point towards visible 3% Inspeck microspheres), the weaker fluorescing 0.3% microspheres are found to be barely visible at both 20 fps and 200 fps (FIGS. 16a and 16c). Despite the fact that faster frame rates result in scaling down the fluorescence captured on the sensor, the autofluorescence and tissue structure are still found to be visible at 200 fps. It is demonstrated that lung autofluorescence may be imaged at 200 fps and possible more. A visualization video illustrating visibility of lung tissue and red 3% Inspeck™ microspheres at 200 fps has been prepared.

Faster frame rates may require faster display hardware (display rate on monitors may currently be limited to 60 Hz to 120 Hz). One interesting observation from a 200 fps video sequence produced in this experiment is the possibility to extend microendoscopic imaging to tissue elastography.

Contrast may often increase with increasing frame rate despite lower fluorescence signal, which may be due to better localization of the object. Slower frame rates may smear the contrast of an object under study due to the fast moving endoscopic environment. To the best of our knowledge, this may be the highest frame rate reported in microendoscopy.

Excised human lung tissue was placed in well plates with five experimental conditions:
1) freshly isolated human monocytes with PKH red (Cellvue® Claret, Sigma Aldrich, USA),
2) freshly isolated human neutrophils with PKH green (PKH67, Sigma Aldrich, USA),
3) *Aspergillus fumigatus* labelled with PKH red,
4) monocytes, neutrophils and fungus (*Aspergillus fumigatus*) together in single well,
5) bacteria (*Pseudomonas aeruginosa*) at $10^7$ CFU/ml labelled in PKH green (PKH67, Sigma Aldrich, USA).

Human tissue was used with regional ethics committee approval retrieved from the periphery of specimens taken from lung cancer resections. Monocytes and neutrophils were isolated and purified from peripheral blood of healthy volunteers. Each sample was imaged for 30 s and the camera settings were as follows: 8 bit image acquisition, gain 24 dB, exposure time 80 ms (12 fps). Well plate 5 with PKH green labelled *Pseudomonas aeruginosa* was additionally imaged at 5 ms exposure time (200 fps) to study the dynamics of fibre core blinking events described below. PKH red and green were used as per manufacturer's instructions.

For both red and green 0.3% Inspeck™ beads, the LOD was determined to be $10^4$ microspheres per ml. Table 3 and Table 4 show that LOD for green and red 0.3% Inspeck™ microspheres embedded in the excised human lung tissue are equivalent to $10^5$ per ml and $10^4$ per ml respectively. The controls show no detected microspheres in both cases.

TABLE 3

Well plate experiment for green 0.3% Inspeck ™ microspheres

| Experiment | Number of duplicate well plates | Number of successful detections |
|---|---|---|
| $10^3$ green 0.3% Inspeck ™ microspheres per ml in lung | 4 | 0 |
| $10^4$ green 0.3% Inspeck ™ microspheres per ml in lung | 4 | 0 |
| $10^5$ green 0.3% Inspeck ™ microspheres per ml in lung | 4 | 2 |
| $10^6$ green 0.3% Inspeck ™ microspheres per ml in lung | 4 | 4 |
| Lung alone | 2 | 0 |
| Distilled water | 2 | 0 |
| $10^6$ empty microspheres per ml in lung | 2 | 0 |
| $10^6$ empty microspheres per ml in distilled water | 2 | 0 |

TABLE 4

Well plate experiment for red 0.3% Inspeck ™ microspheres

| Experiment | Number of duplicate well plates | Number of successful detections |
|---|---|---|
| $10^3$ red 0.3% Inspeck ™ microspheres per ml in lung | 4 | 1 |
| $10^4$ red 0.3% Inspeck ™ microspheres per ml in lung | 4 | 4 |
| $10^5$ red 0.3% Inspeck ™ microspheres per ml in lung | 4 | 4 |
| $10^6$ red 0.3% Inspeck ™ microspheres per ml in lung | 4 | 4 |
| Lung alone | 2 | 0 |
| Distilled water | 2 | 0 |
| $10^6$ empty microspheres per ml in lung | 2 | 0 |
| $10^6$ empty microspheres per ml in distilled water | 2 | 0 |

The higher LOD for green microspheres may be due to a high level of lung tissue autofluorescence in the green. Autofluorescence of the human lung elastin and collagen may enable anatomical navigation between the airways and alveoli. However, once the distal lung is reached, it may be desirable to remove the background autofluorescence if the object we are trying to image has broadly equivalent excitation wavelengths. Lung tissue autofluorescence in the green may be a reason to design molecular probes in red and near-infrared in the lung coupled with microendoscopy as the background fluorescence may drop dramatically with higher wavelengths.

FIGS. 17a, 17b and 17c are images of multiple targets in ex vivo lung tissue. FIG. 17a is an image of lung tissue including monocytes. An example of a monocyte is indicated by arrow 202. FIG. 17b is an image of lung tissue including neutrophils. An example of a neutrophil is indicated by arrow 204. FIG. 17c is an image of lung tissue including fungus (*Aspergillus fumigatus*). The exposure time for the images of FIGS. 17a, 17b, and 17c was set to 80 ms (12 fps), with a gain of 24 dB and an 8 bit image. A video visualisation was also prepared. FIGS. 17a, 17b and 17c may be considered to illustrate the capability of the two-colour widefield system of FIG. 8 to perform fluorescence imaging of multiple targets of immediate relevance to pulmonary inflammation and infection.

In summary, FIG. 17a shows PKH red labelled monocytes in ex vivo lung tissue. FIG. 17b shows PKH green labelled neutrophils in ex vivo lung tissue. FIG. 17c shows strong signal from *Aspergillus fumigatus*. Due to its large size, *Aspergillus fumigatus* may be a relatively easy target to image. Simultaneous detection of monocytes, neutrophils and *Aspergillus fumigatus* has been performed, and was demonstrated in a visualisation video.

As tissue autofluorescence has a strong green component, molecular imaging of targets in green in some circumstances be more difficult than visualisation in other colours. However, for cellular targets 15 µm in size or more, molecular imaging of targets in green may be feasible in some conditions, for example providing that the signal to background is greater than 10%.

Smaller objects such as bacteria may be visible at high signal to background. However the fast moving microendoscopy environment may require a large number of dots for them to be immediately observable by a clinician.

Figure 18A:
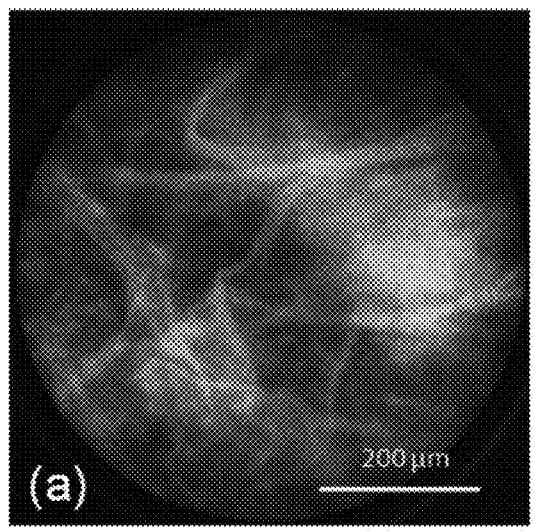
FIGS. 18a and 18b are images of ex vivo lung tissue without and with bacteria respectively.
Figure 18B:
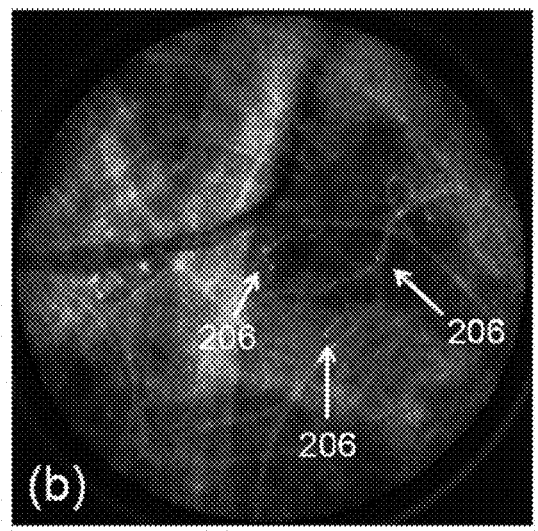

FIGS. 18a and 18b show two images of ex vivo lung, one without bacteria (FIG. 18a) and one with bacteria (FIG. 18b, bacteria indicated by arrows 206). An exposure time was set to 80 ms. Further video visualisations were also prepared, in which bacteria were found to be visible as blinking fluorescing dots. The number of blinking dots was found to be less in a first visualisation video (no bacteria) when compared to a second visualisation video (with bacteria). The first and second visualisation videos were considered to demonstrate bacterial detection via a higher presence of green dots and the blinking of green dots being more obvious where bacteria are present.

Blinking may be explained as follows. If a fluorescing object is smaller than the fibre core and cladding, then the inherent relative motion of the distal end 130 of the fibre bundle 128 with respect to the tissue may induce the object to move in front of the core (causing the object to be visible) and cladding (causing the object not to be visible).

Fibre bundles may be designed in such a way as to increase bacterial blinking. Fibre bundles may be designed in such a way as to improve bacterial detection.

Figure 19A:
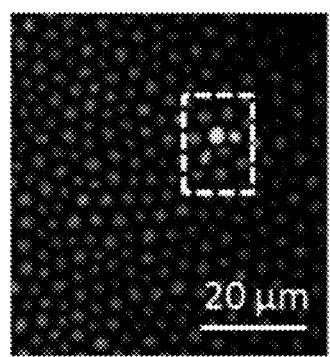
Figure 19C:
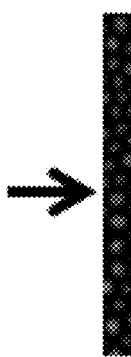

FIGS. 19a to 19c demonstrate this mechanism in three images from another visualisation video. Ex vivo human lung tissue with PKH green labelled *Pseudomonas aeruginosa* was imaged at 200 fps to study the mechanism of blinking in detail. It is suggested that this mechanism may be put to good use providing the bacterial colonies are small enough and bright enough. One may think of engineering fibre cores and cladding (or grids for ex vivo study of assays) to match the size of the object that needs detecting, thus maximizing blinking. In some circumstances, blinking may be readily detectable by observers at SNRs even less than 1. However, it is possible that any object smaller than the fibre cladding will eventually blink whether bacteria or not, so false positives may be likely. Additionally, many bacterial colonies may be large in size (for example, greater than 20 µm). Bacterial colonies that are large in size may not blink.

Although the images of FIGS. 18a to 19b are obtained with the system of FIG. 8, the system of FIG. 1 may also be designed to result in blinking effects, for example by choosing a size of optical fibres in the fibre bundle to be larger than a desired biological target (for example, bacteria).

Autofluorescence may be used for structural imaging in the distal lung. Smartprobes may be deployed to evaluate diagnosis of specific pathology.

In some circumstances, green autofluorescence may interfere with green fluorescing smartprobes. The green autofluorescent signal may have to be disentangled from the green fluorescing smartprobe signal in vivo in situ. In some circumstances, even if the smartprobes are emitting strongly, signal levels in excess of 10% of the background level may be used to perform quantitative assessment. In some circumstances, the non-homogeneous and dynamic nature of the background signal may limit the uniformity of pathology under investigation, which may in some circumstances decrease a limit of detection at the lower limit.

In some circumstances, red and near infrared (NIR) fluorescence may be used. The background in red and/or NIR may be much weaker. In the red and NIR, fluorescence collection efficiency and camera read noise may become limiting. Fluorescence collection efficiency and camera read noise may in some circumstances be improved. For example, an sCMOS camera may be deployed, which may have read noise of less that 1 e$^-$.

In some circumstances, widefield systems may have poorer optical sectional than beam scanned confocal systems. However, as autofluorescence reduces significantly in the near IR, the improved SNR may mean that the reduced optical sectioning of widefield based setups may become increasingly less limiting. The resolution needed may depend on the molecular target. For example, molecular sensing of enzyme activity using a smartprobe displaying fluorescent amplification upon substrate cleavage may not need resolution, just fluorescent detection.

An effect of fibre fluorescence in the red channel when illuminated with 470 nm LED is shown in FIGS. 20a, 20b and 21. The experiment for which results are shown in FIGS. 20a, 20b and 21 comprised imaging the ex vivo lung tissue with 0.3% Inspeck™ beads. Constant 625 nm LED illumination was provided and 470 nm LED was ramped up and down (from 1 mW to 2.4 mW) to illustrate the effect of spectral mixing of red fluorescence of the Alveoflex™ with imaging of Inspeck™ microspheres.

It was found that 1 mW passing through Alveoflex™ causes noticeable red fluorescence, but Inspeck™ 0.3% microspheres are still visible in FIG. 18a (see the zoomed inset in top left of FIG. 18a as well as microspheres indicated by white circles).

FIG. 20a shows 0.3% Inspeck™ microspheres visible against background at 1 mW 470 nm LED illumination.

When 470 nm LED was set to 2.4 mW red fluorescence from the fibre was saturating the red channel of the sensor. FIG. 20b shows 0.3% Inspeck™ microspheres not visible against background at 2.4 mW 470 nm LED illumination. An accompanying video visualisation was prepared.

Figure 19C:
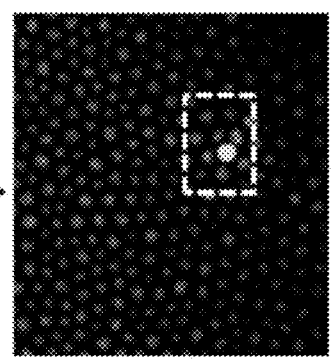

Fluorescence from fibre bundles has been analysed before. FIG. 19 shows a fibre fluorescence spectrum from 500 nm to 850 nm. The spectrum was obtained by using a broad FITC filter-set (FITC-LP01-Clinical-000, Semrock, USA) and spectrometer placed on camera image plane (USB2000 spectrometer, Ocean Optics, USA). Most of the fibre bundle fluorescence is concentrated in the region 600 nm to 700 nm and further work may be carried out to reduce or remove it while keeping multi-colour capability.

No image processing was used in the experiments described above with reference to FIGS. 9 to 21. Instead we focus on the raw performance of the underlying optical system at clinically relevant limits.

It has previously been demonstrated that confocal microendoscopy may benefit from image processing. One image processing methodology is to oversample the fibre core pattern, calculate the signal from each core and interpolate the random core pattern into a rectangular image. This may provide a reliable summary of information from each core. In images described above, the oversampled raw images are presented. Future work may explore image processing techniques to deploy real-time processing for improved multi-colour detection of labelled disease targets.

Measurement results have been presented for system spatial resolution, camera read noise, fluorescence collection, fluorescence spectral throughput, chromatic focus shift An evaluation of high speed performance on ex vivo lung tissue has been presented.

It has been demonstrated that the system of FIG. 8 may provide a fast two-colour widefield fluorescence microendoscopy system capable of simultaneously detecting several disease targets in intact human ex vivo lung tissue. The system has been characterised for light throughput from the excitation light emitting diodes (LEDs), fluorescence collection efficiency and chromatic focal shifts. The effectiveness of the system has been demonstrated by imaging bacteria (*Pseudomonas aeruginosa*) in ex vivo human lung tissue.

A method of bacterial detection through the fibre bundle has been described. The method of bacterial detection uses blinking effects of bacteria as they more in front of the fibre core, providing detection of objects smaller than the fibre core and cladding (for example, around 3 µm). The method of bacterial detection may increase the measured spatial resolution of the system of 4 µm.

Simultaneous imaging of neutrophils, monocytes and fungus (*Aspergillus fumigatus*) in ex vivo human tissue has been shown.

The system of FIG. 8 has been shown to have 10 nanomolar (nM) and 50 nM sensitivity for fluorescein and Cy5 solutions respectively. Lung tissue autofluorescence is shown to remain visible at up to 200 frames per second (fps) camera acquisition rate. The optical system of FIG. 8 may lend itself to clinical translation due to high fluorescence sensitivity, simplicity and the ability to multiplex several pathological molecular imaging targets simultaneously.

Multi-colour fluorescence microendoscopy may in some circumstances provide instant pathology to clinicians during time-limited in vivo in situ interventions. By utilising a simple imaging platform that is designed from off-the-shelf components, it may be readily achievable to detect important pathological targets with little or no image processing. With suitable fluorescent smartprobes it may be possible to disentangle background autofluorescence and derive vital information related to pathology. Low-cost technologies such as LEDs and CMOS sensors are maturing to such an extent that devices such as the system of FIG. 8 may be developed for widespread use.

To understand the processes that commonly cause diseases such as bacterial and fungal infection, microendoscopy is coupled with optical imaging agents. A fast two-colour fluorescence microendoscopy system is demonstrated and characterised in detail for application in distal lung imaging. Bacteria is detected in high quality images and videos demonstrating camera-based two-colour fluorescence endoscopy of excised human lung tissue.

The widefield system of FIG. 8 has been demonstrated to operate in the distal lung by imaging targets ranging in size from 2 µm to 100 µm or more, for example bacterial colonies, monocytes, neutrophils, and the fungus *Aspergillus fumigatus* deposited in ex vivo human alveolar tissue.

Particular embodiments of an endoscopic imaging system have been described above. In further embodiments, features of any of the systems described above may be combined with features of any of the other systems. For example, features of the system of FIG. 1 may be combined with features of the system of FIG. 8.

In particular, although blinking is described in the context of the system of FIG. 8, blinking effects may also be used when imaging using the system of FIG. 1.

We now turn to a further embodiment in which a reflector-dichroic combination is used to enable reflection and fluorescence imaging on the same optical path.

Fluorescence imaging is described above with reference to FIGS. 1 to 21. The fluorescence endoscopy apparatus described above uses a dichroic to separate excitation light and fluorescence. The dichroic may be wavelength selective depending on the direction of incoming light.

In the embodiment of FIG. 1, a multi-band dichroic mirror 26 is used to reflect excitation light from the LEDs 1, 2, 3 into the microscope objective 30. The excitation light causes fluorescence in the imaging region. The fluorescent light returned from the imaging region has a different wavelength to the excitation light. The multi-band dichroic mirror 26 is configured to transmit the fluorescent light received from the imaging region substantially without transmitting excitation light that has been returned from the imaging region, for example due to reflection or scattering. The multi-band dichroic mirror 26 is configured to reflect some wavelength bands (the wavelengths of LEDs 1, 2, 3) while transmitting other wavelength bands (the wavelength of the fluorescent response signals that result from excitation of the imaging region with LEDs 1, 2, 3).

Epi-fluorescence setups may normally illuminate a dichroic in reflectance mode. The returning fluorescence (which may have a higher wavelength) is transmitted through the dichroic and sent to the detector.

Reflection endoscopy is a further type of endoscopy in which reflected light from the imaging region is detected. The reflected light comprises light having wavelengths that are present in the light used for illumination. Reflection endoscopy may usually operate with a light source (for example, one or more LEDs) illuminating the endoscope via a beamsplitter. Reflected light may then be passed to the camera along the same path.

For example, to operate an apparatus similar to that of FIG. 1 in reflection mode, the multi-band dichroic mirror 26 may be replaced with a beamsplitter, for example a 50/50 beamsplitter. The beamsplitter is configured to reflect part of the light from LEDs 1, 2, 3 into the microscope 30, and to transmit part of the reflected light returning from the imaging region. In other embodiments, any suitable beamsplitter may be used to divide light incident on the beamsplitter into two portions.

Figure 22:
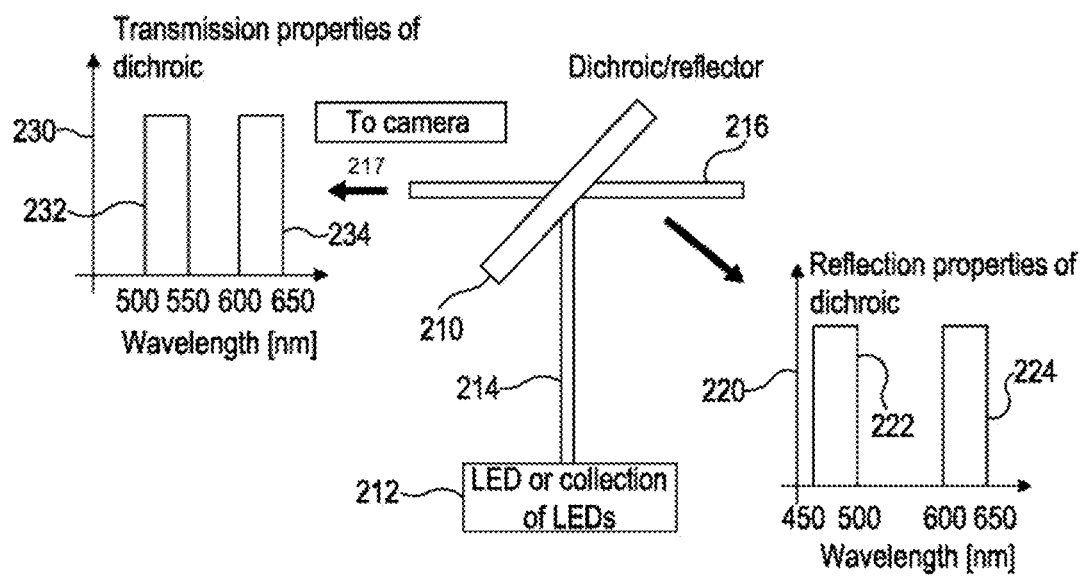
FIG. 22 is a schematic illustration of a dichroic/reflector.

FIG. 22 is a schematic illustration of an embodiment in which the same optical path is used for fluorescence imaging as is used for reflection imaging.

An optical element 210 is configured to act as a 50/50 beamsplitter in first range of wavelengths, by reflecting 50% of the light in the first range of wavelengths and transmitting 50% of the light in the first range of wavelengths. The optical element 210 is configured to act as a dichroic mirror at a second wavelength band, by reflecting substantially all of the light in the second range of wavelengths, and transmitting substantially all of fluorescent light that is produced by excitation light when the excitation light is in the second range of wavelengths. The fluorescent light has a different wavelength from the excitation light that produces it.

The optical element 210 may be referred to as a dichroic/reflector element. In the present embodiment, the optical element 210 is a thin film interference filter that may be used as an epi-fluorescence illuminator in one wavelength band and as a reflector in other bands. The optical element 210 is manufactured using existing thin film interference filter production techniques, for example using at least one of modified magnetron thin film sputtering techniques, sputtered oxide-dielectric coatings, sputtered metal, sputtered metal-dielectric coatings, e-beam and thermal resistive coating. In other embodiments, any suitable method of manufacture may be used.

The optical element 210 provides a single integrated element that is capable of acting both as a beamsplitter and as a dichroic mirror, depending on wavelength.

In FIG. 22, light from one or more LED light sources 212 follows a common optical path depicted as a vertical line 214. The light from the one or more light sources 212 is incident on the optical element 210 at an angle of incidence of 45°. In other embodiments, any suitable angle of incidence may be used.

Plot 220 is a plot of reflection versus wavelength, and shows two wavelength bands 222, 224 in which the optical element 210 is configured to reflect light 217. Wavelength band 222 is at 450 nm to 500 nm. Wavelength band 224 is at 600 nm to 650 nm. In other embodiments, the optical element 210 may be configured to reflect light at any suitable wavelength bands.

Light reflected from optical element 210 follows an optical path indicated by horizontal line 216 in FIG. 22 and illuminates an imaging region (not shown). Light is returned from the imaging region along line 216 and is incident on the optical element 210.

Plot 230 is a plot of transmission versus wavelength, and shows two wavelength bands 232, 234 in which the optical element 210 is configured to transmit light. Wavelength band 232 is at 500 to 550 nm. Wavelength band 234 is at 600 to 650 nm. In other embodiments, the optical element 210 may be configured to transmit any suitable wavelengths.

When illuminated by light in the 600 nm to 650 nm band, the optical element 210 acts as a beamsplitter. It both reflects and transmits light in the 600 to 650 nm wavelength band. In the present embodiment, the ratio of transmission to reflection is 50/50. In other embodiments, any ratio may be used. The beamsplitter may divide light that is incident upon it into two portions of any appropriate size.

When illuminated by light in the 450 nm to 500 nm band, the optical element 210 acts as a dichroic mirror. It reflects light in the 450 nm to 500 nm wavelength band, and transmits light in the 500 nm to 550 nm band 234.

By providing a single filter that acts as a dichroic mirror at some wavelengths and as a beamsplitter at other wavelengths, microendoscopy may be performed in fluorescence mode for selected wavelength bands and reflection mode in other complementary bands.

The same optical path may be used for fluorescence imaging as is used for reflection imaging. The use of the same optical path for both fluorescence and reflection imaging may result in a compact and/or cost effective imaging apparatus having increased functionality.

FIG. 22 above shows a red band to be reflective and a green band to be epi-fluorescent. In other embodiments, other bands may be reflective or fluorescent.

Figure 23:
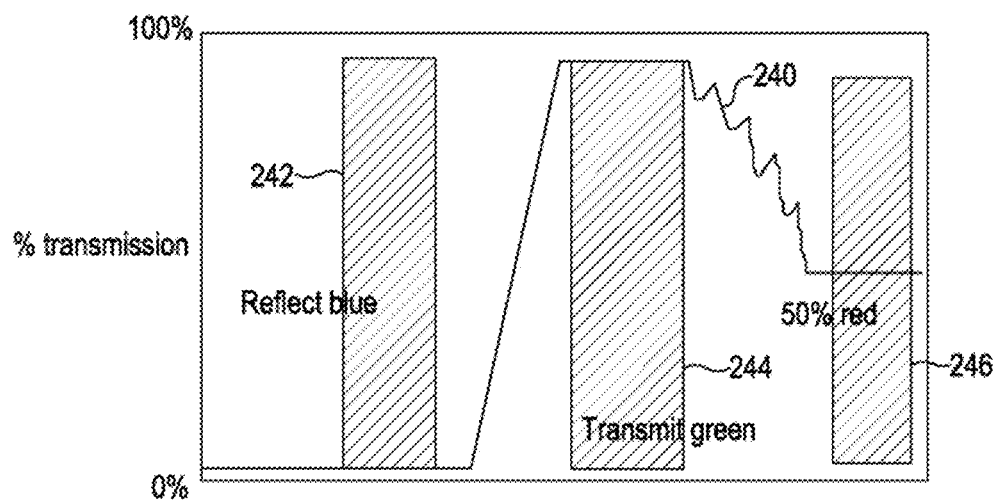
FIG. 23 is a plot of transmission for three wavelength bands.

FIG. 23 is a schematic plot of transmission versus wavelength for an optical element. Line 240 shows the transmission profile of the optical element. At a first wavelength band 242 comprising blue light, the transmission of the optical element is very low, for example less than 10%, less than 5% or a negligible amount. At a second wavelength band 244 comprising green light, the transmission of the optical element is high, for example greater than 90%. At a third wavelength band 246 comprising red light, transmission is 50%. Therefore in blue and green the optical element acts as a dichroic, whereas in red the optical element acts as a beamsplitter.

We have demonstrated above three-colour fluorescence widefield microendoscopy, for example using the apparatus of FIG. 1.

In a further embodiment, one band of the apparatus of FIG. 1 is chosen to be reflective. For example, the NIR band may be chosen to be reflective if fluorescence targets are red and green. The multi-band dichroic of FIG. 1 is replaced with an optical element that is configured to act as a reflector for the NIR band and as a dichroic for the remaining bands.

In further embodiments, any combination of wavelength bands may be used for fluorescence imaging and for reflection imaging.

In another embodiment, one of the LEDs 1, 2, 3 of FIG. 1 is replaced with a white LED. The multi-band dichroic 26 of FIG. 1 is replaced with an optical element that is configured to reflect and transmit white light. White light endoscopy is performed using the white LED as a light source. NIR is kept as a fluorescent band.

Other changes may be made to the apparatus of FIG. 1, for example by changing dichroics 20, 22 and/or filters 24, 50 to correspond to the wavelengths used.

The simplicity of a multi-band architecture described above (for example, with relation to FIG. 1) may be kept while introducing the feature of reflection endoscopy by using an appropriate filter and appropriate light sources. Reflection endoscopy and fluorescence endoscopy may be performed using a common optical path. One set of sources and one camera may be used to provide an apparatus that is capable of performing both reflection imaging and fluorescence imaging.

In some circumstances, the camera gain and/or other camera settings may be changed when switching from reflected light to fluorescent light. In some embodiments, camera gain may be set to auto (an automatic mode). When set to auto, the camera may adapt gain to light level.

In some embodiments, fluorescence imaging and reflection imaging are time-interleaved. The timing-interleaving of the light sources may be performed as described above.

In other embodiments, the apparatus may be used in a non-time-interleaved mode, in which reflector mode imaging is used for a period of time (for example, to capture a succession of images) and fluorescence mode imaging is then used for a further period of time. The periods of time may be, for example, of the order of seconds or longer. In some circumstances, it may be preferred to set camera settings for fluorescence or for reflection without constantly changing them. This may depend on camera firmware flexibility.

Features of embodiments described above may be combined with features of other embodiments. For example, features of embodiments in which all colours of excitation signals are used for fluorescence imaging may be combined with features of embodiments in which some colours of excitation signals are used for fluorescence imaging and others are used for reflection imaging.

Embodiments described above are used to perform imaging (and optionally spectroscopy) of the distal lung. Further embodiments may be used to perform imaging of any suitable anatomical region, for example any anatomical region that is capable of being accessed via an endoscope. For example, embodiments may be used to perform imaging of the bronchus, gastrointestinal tract, or urinary tract. Imaging may be performed on any suitable human or animal subject. Imaging may be performed for any suitable medical or veterinary application.

Although the use of particular smartprobes is described above, in other embodiments any suitable fluorescent material may be introduced into the imaging region, for example any suitable dye, stain or probe. Light sources may be chosen to excite the or each fluorescent material. By using fluorescent materials, information may be obtained about tissue structure and also about molecular signals at other wavelengths.

It may be understood that the present invention has been described above purely by way of example, and that modifications of detail can be made within the scope of the invention.

Each feature disclosed in the description and (where appropriate) the claims and drawings may be provided independently or in any appropriate combination.

The invention claimed is:

1. An endoscopic imaging apparatus comprising:
    an optical fibre bundle comprising a plurality of fibre cores for use in imaging, the optical fibre bundle being configured to transmit excitation signals from a proximal end to a distal end of the optical fibre bundle via the plurality of fibre cores and to transmit response signals from the distal end to the proximal end of the optical fibre bundle via the plurality of fibre cores, wherein the optical fibre bundle has a diameter of less than 2 mm, and wherein the optical fibre bundle is configured to be inserted through and deployed from a working channel of an endoscope;
    at least one light source coupled to the proximal end of the optical fibre bundle and configured to provide excitation signals to an imaging region at or near a distal end of the optical fibre bundle and via the plurality of fibre cores, each excitation signal having one of a plurality of different colours;
    a controller configured to control the at least one light source to provide the excitation signals as a repeating time-interleaved sequence that comprises at least an excitation signal of a first one of the colours and a subsequent excitation signal of a second one of the colours, wherein each of the excitation signals occupies a respective time interval of between 5 ms and 500 ms;
    a monochrome detector;
    a further detector other than the monochrome detector;
    a beamsplitter configured to receive a respective response signal for each of the excitation signals, and to split the respective response signal such as to send a first proportion of the respective response signal to the monochrome detector and to send a second proportion of the respective response signal to the further detector, such that the light received by the further detector corresponds to the light received at the monochrome detector; and
    an optical element configured to reflect at least part of each of the excitation signals towards the imaging region, and, for each of the excitation signals, to receive a respective response signal emitted from the imaging region and transmitted from the distal end to the proximal end of the optical fibre bundle via the plurality of fibre cores, and to transmit the respective response signals to the beamsplitter,
    wherein:
        the monochrome detector is configured to receive the first proportion of each respective response signal emitted from the imaging region and to generate image data using the first proportion of the response signal;

the further detector is configured to receive the second proportion of each respective response signal and to generate further data using the second proportion of the response signal;

the generating of the image data using the monochrome detector is synchronized with the time intervals of the excitation signals of the repeating time-interleaved sequence, and the optical element is configured to act as a dichroic mirror for a first range of wavelengths comprising at least one of the plurality of colours, and to act as a beamsplitter for a second, different range of wavelengths comprising at least one other of the plurality of colours.

2. The apparatus according to claim 1, wherein the further detector comprises at least one of a spectrometer, a time resolved detector, or a fluorescence lifetime imaging (FLIM) detector.

3. The apparatus according to claim 1, wherein the monochrome detector or the further detector comprises a fluorescence lifetime imaging (FLIM) detector configured both to generate said image data and to perform fluorescence lifetime imaging.

4. The apparatus according to claim 1, wherein each excitation signal comprises pulsed and/or modulated light, and wherein the monochrome detector or the further detector comprises a time-resolved detector configured, for each excitation signal, to perform fluorescence lifetime imaging (FLIM) of the first proportion or the second proportion of the response signal emitted from the imaging region in response to the excitation signal.

5. The apparatus according to claim 1, wherein the further detector comprises at least one of a time-resolved camera, a time-gated intensified CCD camera, a time-gated intensified sCMOS camera, a CMOS SPAD array, a modulateable camera.

6. The apparatus according to claim 1, wherein, for each excitation signal, the further detector is configured to determine at least one fluorescence lifetime.

7. The apparatus according to claim 1, wherein the at least one light source is configured to provide modulated light and the further detector is configured to perform modulated FLIM.

8. The apparatus according to claim 1, wherein the further detector comprises a spectrometer, each excitation signal comprises pulsed and/or modulated light, and the spectrometer is configured to perform time-resolved spectroscopy.

9. The apparatus according to claim 1, further comprising at least one filter arranged to filter said at least part of the response signal or said further part of the response signal.

10. The apparatus according to claim 9, wherein the at least one filter comprises a variable filter synchronised with operation of the at least one light source and/or the monochrome detector or the further detector to provide different filtering for the response signals obtained from the excitation signals of different colours.

11. The apparatus according to claim 1, wherein the plurality of different colours are distributed over a wavelength range of one of: greater than 100 nm, or greater than 250 nm, or greater than 400 nm.

12. The apparatus according to claim 1, further comprising a computer processor configured to provide imaging in each of the plurality of different colours at a frame rate of between 0.1 fps and 400 fps.

13. The apparatus according to claim 1, further comprising a computer processor configured to produce at least one image data set representative of at least one image from the image data, and wherein the at least one image comprises a single image that is based on image data obtained from a plurality of the response signals obtained in response to the excitation signals of different colours.

14. The apparatus according to claim 1, further comprising a computer processor configured to produce at least one image data set representative of at least one image from the image data, wherein the at least one image data set is representative of a combination of image data from the further detector and FLIM data or spectroscopy data.

15. The apparatus according to claim 1, further comprising at least one aperture element configured to select a part of a field of view of the apparatus, wherein the image data is representative of an image of the selected part of the imaging region.

16. The apparatus according to claim 1, wherein the optical fibre apparatus is configured to perform contact imaging.

17. The apparatus according to claim 1, wherein the distal end of the optical fibre apparatus is configured for attachment of a droplet, the droplet comprising at least one of tissue, fluorescent material.

18. The apparatus according to claim 1, further comprising an optical element positioned in the common transmission path and configured to reflect at least part of each of the excitation signals towards the imaging region, and to transmit at least part of each of the response signals to the detector.

19. The apparatus according to claim 1, wherein the apparatus is configured to perform fluorescence imaging using excitation signals having the at least one of the plurality of colours, and to perform reflection imaging using excitation signals having the at least other one of the plurality of colours.

20. An endoscopic imaging method comprising:
providing, by at least one light source, excitation signals to an imaging region, each excitation signal having one of a plurality of different colours, the at least one light source being coupled to a proximal end of an optical fibre bundle and the imaging region being at or near a distal end of the optical fibre bundle, the optical fibre bundle comprising a plurality of fibre cores for use in imaging, the optical fibre bundle being configured to transmit excitation signals from a proximal end to a distal end of the optical fibre bundle via the plurality of fibre cores and to transmit response signals from the distal end to the proximal end of the optical fibre bundle via the plurality of fibre cores, wherein the optical fibre bundle has a diameter of less than 2 mm, and wherein the optical fibre bundle is configured to be inserted through and deployed from a working channel of an endoscope;
controlling, by a controller, the at least one light source to provide the excitation signals as a repeating time-interleaved sequence that comprises at least an excitation signal of a first one of the colours and a subsequent excitation signal of a second one of the colours, wherein each of the excitation signals occupies a respective time interval of between 5 ms and 500 ms;
reflecting, by an optical element, at least part of each of the excitation signals towards the imaging region, and, for each of the excitation signals, receiving, by the optical element, a respective response signal emitted from the imaging region and transmitted from the distal end to the proximal end of the optical fibre bundle via the plurality of fibre cores, and transmitting, by the optical element, the respective response signals to a beamsplitter, wherein the optical element is configured to act as a dichroic mirror for a first range of wavelengths comprising at least one of the plurality of colours, and to act as the beamsplitter for a second, different range of wavelengths comprising at least one other of the plurality of colours;

receiving, by the beamsplitter, a respective response signal for each of the excitation signals;

splitting, by the beamsplitter, the respective response signal such as to send a first proportion of the respective response signal to a monochrome detector and to send a second proportion of the respective response signal to a further detector, such that the light received by the further detector corresponds to the light received at the monochrome detector;

receiving, by the monochrome detector, the first proportion of each respective response signal emitted from the imaging region in response to the excitation signal;

generating, by the monochrome detector, image data using the first proportion of the response signal, wherein the generating of the image data using the monochrome detector is synchronized with the time intervals of the excitation signals of the repeating time-interleaved sequence;

receiving, by the further detector, the second proportion of each respective response signal; and generating, by the further detector, further data using the second proportion of the response signal.

21. An endoscopic imaging apparatus comprising:

at least one light source configured to provide excitation signals to an imaging region via a common transmission path, each excitation signal having one of a plurality of different colours, in which at least one of the different colours has a wavelength in a first excitation wavelength band and at least a further one of the different colours has a wavelength in a second excitation wavelength band which does not overlap with the first excitation wavelength band, the at least one light source being coupled to a proximal end of an optical fibre bundle and the imaging region being at or near a distal end of the optical fibre bundle, the optical fibre bundle comprising a plurality of fibre cores for use in imaging, the optical fibre bundle being configured to transmit excitation signals from a proximal end to a distal end of the optical fibre bundle via the plurality of fibre cores and to transmit response signals from the distal end to the proximal end of the optical fibre bundle via the plurality of fibre cores;

a controller configured to control the at least one light source to provide the excitation signals;

a detector configured, for each of at least some of the excitation signals, to receive at least part of a respective response signal emitted from the imaging region in response to the excitation signal and to generate image data based on the at least part of the response signal; and an optical element positioned in the common transmission path and configured to:

for each excitation signal having a wavelength within the first excitation wavelength band, reflect more than 90% of the excitation signal towards the imaging region, and transmit more than 90% of a fluorescence response signal emitted from the imaging region, wherein the fluorescence response signal corresponds to fluorescent light produced in response to excitation of the imaging region by the excitation signal, and wherein the response signal has a wavelength signal within a fluorescence wavelength band which is different from the first excitation wavelength band; and for each excitation signal having a wavelength within the second excitation wavelength band, reflect between 40% and 60% of the excitation signal towards the imaging region and transmit between 60% and 40% of the excitation signal.

22. The apparatus according to claim 21, wherein the optical element is configured to act as a dichroic mirror for a first range of wavelengths comprising at least one of the plurality of colours, and to act as a beamsplitter for a second, different range of wavelengths comprising at least one other of the plurality of colours.

23. The apparatus according to claim 21, wherein the apparatus is configured to perform fluorescence imaging using excitation signals having the at least one of the plurality of colours, and to perform reflection imaging using excitation signals having the at least other one of the plurality of colours.

* * * * *